United States Patent [19]

Toivola et al.

[11] Patent Number: 4,696,949
[45] Date of Patent: Sep. 29, 1987

[54] NOVEL TRI-PHENYL ALKANE AND ALKENE DERIVATIVES AND THEIR PREPARATION AND USE

[75] Inventors: Reijo J. Toivola; Arto J. Karjalainen, both of Oulu; Kauko O. A. Kurkela, Oulu; Marja-Liisa Soderwall, Oulu; Lauri V. M. Kangas, Turki; Guillermo L. Blanco, Oulu; Hannu K. Sunduiqst, Kaarina, all of Finland

[73] Assignee: Farmos Group Ltd., Turku, Finland

[21] Appl. No.: 823,856

[22] Filed: Jan. 29, 1986

Related U.S. Application Data

[63] Continuation of Ser. No. 497,813, May 25, 1983, abandoned.

[30] Foreign Application Priority Data

Jun. 25, 1982 [GB] United Kingdom ............... 8218414

[51] Int. Cl.[4] ................... A61K 31/135; C07C 91/06
[52] U.S. Cl. .................................. 514/648; 564/324; 564/299; 514/644
[58] Field of Search ................ 564/324, 299; 514/644

[56] References Cited

FOREIGN PATENT DOCUMENTS 1015787 1/1966 United Kingdom .

OTHER PUBLICATIONS

Catlaneo et al., Farmaco 15 1960; pp. 632-641.
Xn et al., Acta Pharmaceutica Sinica 15 (11) 1980, pp. 648-655
Curtin et al., J. Amer. Chem. Soc. 77, 1955, pp. 4566-4570.
Koelach, J.A.C.S. 54 1932; pp. 2045-2048.
Hassner et al., J. Org. Chem. 36 (15) 1971; pp. 2176-2180.
Hassner et al., J. Org. Chem. 35 (10) 1970; pp. 3397-3401.
Normen et al., J. Chem. Soc. B 1967 (6), pp. 598-604.
Simamura et al., Bull. Chem. Soc. Japan 27 1954; pp. 231-235.
Polman et al., Recl. Trav. Chim. Pays. Bas 92, 1973; pp. 845-854.
Bergnener et al., Ber. 66B; 1933; pp. 54-58.
Bonner, J. Amer. Chem. Soc. 81, 1954; pp. 1181-1183.
Norman et al., J. Chem. Soc. B 1967 (6), pp. 604-611.
Dormon et al., Ber. Jahrg, 87. 5 1954, p. 630.
Yaulx et al., J. Org. Chem. 30 (1) 1965, pp. 58-60.
Muihailovic et al., Tetrahedron 1978, 34(16), pp. 2587-2589.

(List continued on next page.)

Primary Examiner—Nicky Chan
Attorney, Agent, or Firm—Armstrong, Nikaido, Marmelstein & Kubovcik

[57] ABSTRACT

The invention provides novel compounds of the formula:

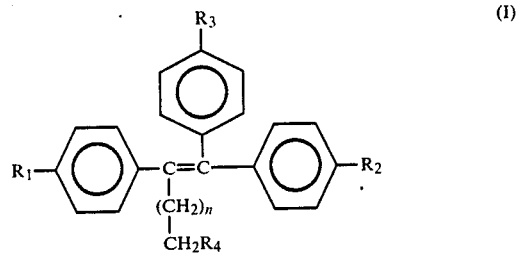

and

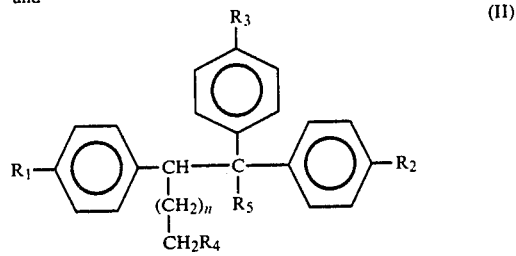

wherein n is 0 to 4, $R_1$ and $R_2$, which can be the same or different are H, OH, alkoxy of 1 to 4 carbon atoms, benzyloxy or methoxymethoxy; $R_3$ is H, OH, halogen, alkoxy of 1 to 4 carbon atoms, benzyloxy, methoxymethoxy, 2,3-dihydroxypropoxy or

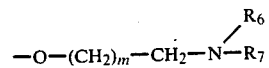

wherein m is 1 or 2, $R_6$ and $R_7$, which can be the same or different are H or an alkyl group of 1 to 4 carbon atoms, or

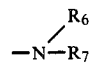

can form an N-containing three-, four-, five- or six-membered heterocyclic ring; $R_4$ is OH, F, Cl, Br, I, mesyloxy, tosyloxy, alkylcarbonyloxy of 1 to 4 C-atoms, formyloxy or $CH_2R_4$ is replaced by CHO; $R_5$ is H or OH; or $R_4$ and $R_5$ together form an —O— bridge between the carbon atoms to which they are attached, and their non-toxic pharmaceutically acceptable salts and esters and mixtures thereof. Processes for the preparation of these compounds are described, and also novel pharmaceutical compositions containing them. These compounds exhibit valuable pharmacological properties as estrogenic, anti-estrogenic, and progestanic agents. They are also effective against oestrogen-dependent tumors. Certain compounds are useful as chemical intermediates for the preparation of pharmacologically active compounds of the invention.

7 Claims, No Drawings

OTHER PUBLICATIONS

Hauptmann et al., J. Prakt. Chem. 19, 1963; pp. 175–179.
"Tamoxifen", cited in the Merck Index, pp. 1711 and 1172, 9th Edition.
Pollard et al., Steroids, 11, 1968, pp. 897–907.
Sutherland et al., Molecular & Cell Endoc., 25, (1982) EP 5-23.
Black et al., Life Sciences, 26, 1980, pp. 1453–1458.
Namer et al., Cancer Res., 40, 1980, pp. 1750–1752.
Markaverich et al., J. Steroid Biochem., 14, 1980, pp. 125–132.
Dix et al., Endocrinology, 1980, pp. 2011–2020.
Jordan et al., J. Steroid Biochem., 1979, pp. 285–291.

NOVEL TRI-PHENYL ALKANE AND ALKENE DERIVATIVES AND THEIR PREPARATION AND USE

This application is a continuation of application Ser. No. 497,813, filed May 25, 1983, now abandoned.

The present invention relates to tri-phenyl-alkane and alkene derivatives and their non-toxic pharmaceutically acceptable salts and esters, and their preparation, to pharmaceutical compositions containing the same and to their use.

The compounds of the present invention have the general formula:

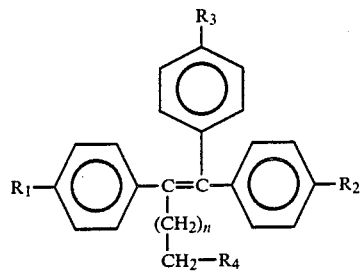
(I)

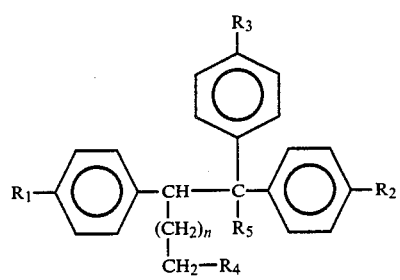
(II)

wherein n is 0 to 4, $R_1$ and $R_2$, which can be the same or different are H, OH, an alkoxy group of 1 to 4 carbon atoms, benzyloxy or methoxymethoxy; $R_3$ is H, OH, halogen, alkoxy of 1 to 4 carbon atoms, benzyloxy, methoxymethoxy, 2,3-dihydroxypropoxy or

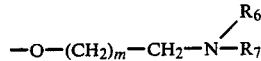

wherein m is 1 or 2, $R_6$ and $R_7$, which can be the same or different are H or an alkyl group of 1 to 4 carbon atoms, or

can form an N-containing three-, four-, five- or six-membered heterocyclic ring; $R_4$ is OH, F, Cl, Br, I, mesyloxy, tosyloxy, alkylcarbonyloxy of 1 to 4 carbon atoms, formyloxy or $CH_2R_4$ is replaced by CHO; $R_5$ is H or OH; or $R_4$ and $R_5$ together form an —O— bridge between the carbon atoms to which they are attached, and their non-toxic pharmaceutically acceptable salts and esters and mixtures thereof provided that (a) when n is 0, then $R_2$ and $R_3$ are not both simultaneously hydrogen or methoxy (b) when n is 0, then $R_3$ must be other than halogen (c) when n is 1 and $R_4$ and $R_5$ both are OH or together form an —O— bridge between the carbon atoms to which they are attached, then $R_1$, $R_2$ and $R_3$ are not all simultaneously hydrogen (d) when n is 2 and $R_4$ and $R_5$ together form an —O— bridge between the carbon atoms to which they are attached, then $R_1$, $R_2$ and $R_3$ are not all simultaneously hydrogen.

A characteristic feature of the compounds of the invention is the functional group $R_4$ attached to the end of the alkyl side chain of the triphenylethene or the triphenylethane skeleton.

A preferred class of compounds of formula (I) or (II) are those wherein each of $R_1$, $R_2$ and $R_3$ is hydrogen, hydroxy, methoxy or ethoxy, at least one of $R_1$, $R_2$ and $R_3$ being other than hydrogen, and $R_3$ may in addition be

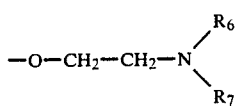

where $R_6$ and $R_7$ are methyl or ethyl, $R_4$ is chlorine, bromine or hydroxy, $R_5$ is hydrogen or hydroxy, or $R_4$ and $R_5$ together form an —O— bridge between the carbon atoms to which they are attached, and its non-toxic pharmaceutically acceptable salts and esters and mixtures thereof.

Preferred heterocyclic rings, when $R_4$ and $R_5$ together form an —O— bridge between the carbon atoms to which they are attached, are the tetrahydrofuran and tetrahydropyran rings. If

forms a heterocyclic ring, preferred radicals are for example aziridinyl, pyrrolidinyl, piperidino or morpholino radicals.

Preferred compounds of the invention are for example:
1-phenyl-1,2-bis(4-hydroxyphenyl)-1-buten-4-ol
4-bromo-1-phenyl-1,2-bis(4-hydroxyphenyl)-1-butene
2-phenyl-2,3-bis(4-hydroxyphenyl)tetrahydrofuran
1,2-diphenyl-1-(4-hydroxyphenyl)-1-penten-5-ol
2,3-diphenyl-2-(4-hydroxyphenyl)tetrahydropyran
1,2-diphenyl-1-(4-hydroxyphenyl)-1-penten-5-al
1,2-diphenyl-1-(4-hydroxyphenyl)-1-buten-4-ol
2,3-diphenyl-2-(4-hydroxyphenyl)tetrahydrofuran
1,2-diphenyl-1-[4-[2-(N,N-dimethylamino)ethoxy]-phenyl]-1-buten-4-ol
4-chloro-1,2-diphenyl-1-[4-[2-(N,N-dimethylamino)ethoxy]phenyl]-1-butene
4-chloro-1,2-diphenyl-1-[4-[2-(1-aziridinyl)ethoxy]-phenyl]-1-butene
4-bromo-1,2-diphenyl-1-[4-[2-(1-pyrrolidinyl)ethoxy]-phenyl]-1-butene
2,3-diphenyl-2-[4-[2-(N,N-diethylamino)ethoxy]-phenyl]tetrahydrofuran
1-phenyl-1,2-bis(4-hydroxyphenyl)butan-4-ol
4-bromo-1-phenyl-1,2-bis(4-hydroxyphenyl)butane
1,2-diphenyl-1-(4-hydroxyphenyl)butan-4-ol
4-chloro-1,2-diphenyl-1-[4-(2-piperidinoethoxy)-phenyl]butane
1,2-diphenyl-1-(4-hydroxyphenyl)butane-1,4-diol
1-phenyl-1,2-bis(4-hydroxyphenyl)butane-1,4-diol
1,2-diphenyl-1-(4-methoxyphenyl)-1-buten-4-ol 4-bromo-1,2-diphenyl-1-[4-[2-(N,N-dimethylamino)ethoxy]phenyl]-1-butene 4-chloro-1,2-diphenyl-1-(4-hydroxyphenyl)butane 4-chloro-1,2-diphenyl-1-(4-hydroxyphenyl)-1-butene 1,2-diphenyl-1-[4-[2-(N,N-dimethylamino)ethoxy]phenyl]butane-1,4-diol The invention encompasses pure (Z)- and (E)-isomers of the compounds and mixtures thereof as well as pure (RR,SS)- and (RS,SR)-enantiomer couples and mixtures thereof.

The invention includes pharmaceutically acceptable salts of aminosubstituted compounds with organic and inorganic acids, for example citric acid and hydrochloric acid. The invention also includes quaternary ammonium salts, for example methoiodide- and benzochloride salts, as well as N-oxides which can be prepared from the amino-substituted compounds.

Pharmaceutically acceptable salts can also be prepared from the phenolic compounds by treatment with inorganic bases, e.g. sodium hydroxide. Also esters of the phenolic compounds can be made with aliphatic and aromatic carboxylic acids, e.g. acetic acid and benzoic acid esters.

The compounds of the invention possess pharmacologically valuable properties because of their estrogenic, antiestrogenic or progestanic effects. Thus the compounds are useful for the purposes where such effects are desired.

The compounds of the invention are active against hormone-dependent tumours and are especially valuable in the treatment of breast tumours.

According to a feature of the invention, the compounds of formula (I) or (II) can be prepared by a process which, in general terms, comprises reacting a compound of the formula:

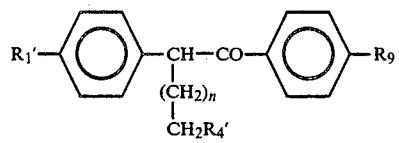

wherein n is as hereinbefore defined, $R_1'$ is the same as $R_1$ as hereinbefore defined or is a hydroxyl group protected as a mixed acetal group, $R_4'$ is the same as $R_4$ as hereinbefore defined or is a protected such group, and $R_9$ is a group $R_2$ or $R_3$ as hereinbefore defined or is a hydroxyl group protected as a mixed acetal group, with an organic-metallic compound of the formula:

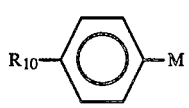

wherein M is —MgHal or —Li and $R_{10}$ is a group $R_2$ or $R_3$ as hereinbefore defined or is a hydroxyl group protected as a mixed acetal group, to give a compound of the formula:

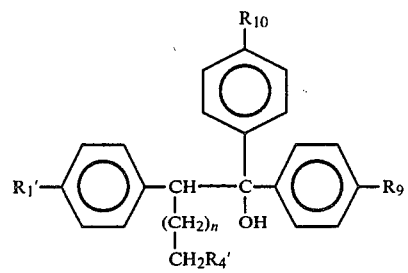

which is then treated, if necessary, to convert the radicals $R_1'R_4'R_9$ and $R_{10}$ into the radicals $R_1$, $R_2$, $R_3$ and $R_4$ to provide a compound of formula II in which $R_5$ is hydroxyl, and optionally dehydrating the product to give a compound of formula I, or treating the product to provide a compound of formula II in which $R_5$ is other than hydroxyl, or one in which $R_4$ and $R_5$ together form an —O— bridge, and/or optionally treating the product to convert a radical $R_1$, $R_2$, $R_3$, $R_4$ or $R_5$ into another such radical as hereinbefore defined and/or optionally treating the product to convert it into a non-toxic pharmaceutically acceptable salt, N-oxide or ester thereof.

This process may be operated in a variety of ways. For example, a desoxybenzoin or desoxybenzoin derivative of the formula:

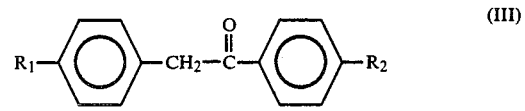

(III)

wherein $R_1$ and $R_2$, which can be the same or different, are as defined before or mixed acetal, for example (tetrahydropyran-2-yl)oxy, can be alkylated with a protected haloalcohol of the formula:

$$hal-(CH_2)_nCH_2OR_8 \qquad (IV)$$

wherein hal is halogen, n is as defined before and $OR_8$ is either a mixed acetal, as (tetrahydropyran-2-yl)oxy, or benzyloxy to give a protected diphenyloxoalkanol of the formula

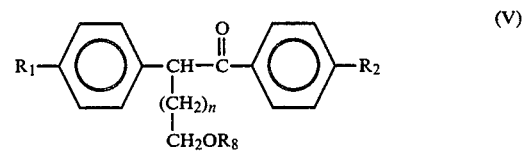

(V)

wherein $R_1$ and $R_2$ are as defined before or mixed acetal, $R_8$ and n are as above. The last mentioned compound is further reacted by a Grignard reaction with a phenylmagnesiumhalide derivative of the formula

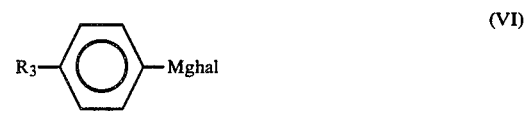

(VI)

or with a corresponding lithium compound of the formula

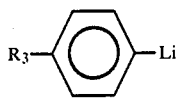

(VII)

wherein $R_3$ in the compounds VI and VII is as defined before or a mixed acetal, as (tetrahydropyran-2-yl)oxy. This reaction gives a protected triphenyldiol of the formula

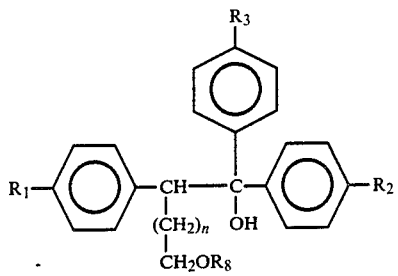

(VIII)

wherein $R_1$, $R_2$ and $R_3$ are as defined before or mixed acetal and $R_8$ and n are as above.

By interchange of the groups $R_2$ and $R_3$ of the intermediate (V) and the reagents (VI) or (VII) the same protected triphenyldiol is obtained. If $OR_8$ is a mixed acetal, the protecting group $R_8$ can be removed for example by an appropriate acid catalyst in the presence of water.

Simultaneously, any mixed acetal protecting group in a phenyl ring will be removed. The reaction gives a triphenyldiol of the formula

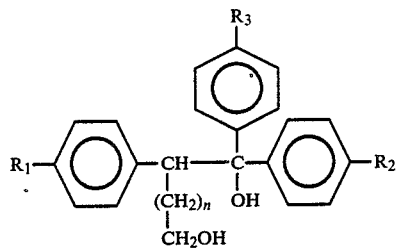

(IX)

wherein $R_1$, $R_2$, $R_3$ and n are as defined before. The triphenyldiol (IX) is dehydrated for example by an appropriate acid catalyst, either in the presence of water or under dry conditions. Depending on the reaction conditions and the value of n, the reaction gives either a triphenylcyclo-oxa-alkane of the formula

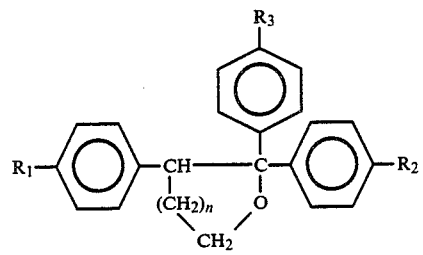

(X)

or a triphenylalkenol of the formula

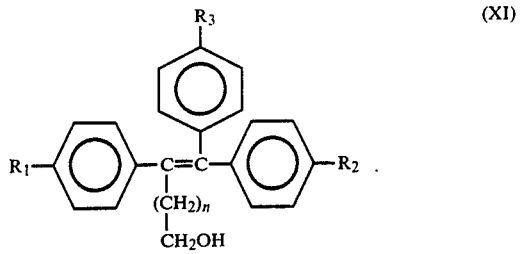

(XI)

or a mixture thereof, wherein $R_1$, $R_2$, $R_3$ and n are as defined before.

By combining the removal of the protecting group and the dehydration, the triphenylcyclo-oxa-alkane (X) or the triphenylalkenol (XI) or a mixture thereof can be obtained in one single step from the protected triphenyldiol (VIII). By choice of appropriate conditions the triphenylalkenol (XI) can be obtained also from the triphenylcyclo-oxa-alkane (X). The benzyl group ($R_8$) is preferably removed from the protected triphenyldiol (VIII) by catalytic hydrogenation. Then by choice of suitable conditions, the same products (IX–XI) can be obtained as were obtained by removal of the mixed acetal group. Simultaneously a possible benzyl protecting group in the phenyl ring will be removed.

The removal of the protecting group from the protected triphenyldiol (VIII) and the dehydration can also be performed in the reverse order as follows: First the protected triphenyldiol (VIII) is dehydrated, for example with a mixture of acid anhydride and acid chloride to give a protected triphenylalkenol of the formula

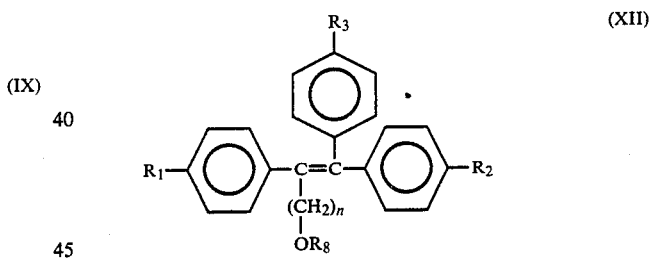

(XII)

wherein $R_1$, $R_2$ and $R_3$ are as defined before or mixed acetal, and $R_8$ and n are as above. Then the mixed acetal or ether protecting group is removed as described above to give the triphenylalkenol (XI).

Desoxybenzoin or a desoxybenzoin derivative (III) can be alkylated also with an unprotected haloalcohol (IV), wherein $R_8$ is hydrogen, to give an unprotected diphenyloxoalkanol (V), wherein $R_8$ is hydrogen. In a further reaction the unprotected diphenyloxoalkanol (V) is reacted with a phenylmagnesiumhalide derivative (VI) or with a corresponding lithium compound (VII). This reaction gives an unprotected triphenyldiol (VIII), wherein $R_8$ is hydrogen. The same unprotected triphenyldiol is obtained by interchange of the groups $R_2$ and $R_3$ of the intermediate and reagent. Dehydration as well as the removal of a possible mixed acetal protecting group from the phenyl ring can be performed by an adaptation of the processes described above.

Another process for the preparation of the compounds of the invention comprises hydroalumination of a "styrene"-derivative of the formula

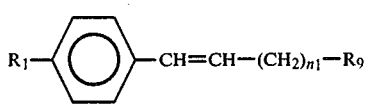

(XIII)

wherein $R_1$ is as defined before, $n_1$ is 0 to 3 and $R_9$ is —CHO, —CH$_2$OH, —COOH or the corresponding ester, with an aluminium hydride reduction agent, for example lithium aluminium hydride, to give an Al-complex of the formula

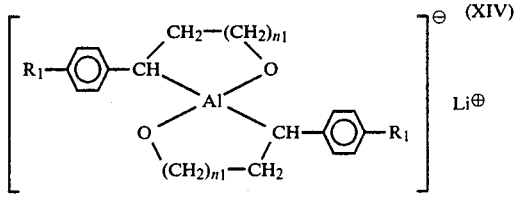

(XIV)

wherein $R_1$ and $n_1$ are as defined before.

Reacting this complex with a benzophenone derivative of the formula

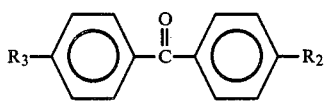

(XV)

wherein $R_2$ and $R_3$ are the same as defined before gives, in one step, the triphenyldiol (IX). Reacting this with, for example, a carboxylic acid anhydride of the formula

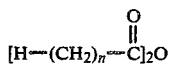

(XVI)

wherein n is as above, or the corresponding carboxylic acid, results in esterification of the primary hydroxyl group, and gives a triphenyldiol ester of the formula

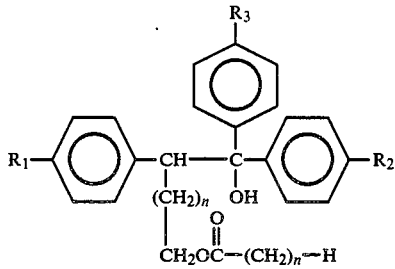

(XVII)

wherein $R_1$, $R_2$, $R_3$ and n are as defined before. This ester may then be dehydrated, for example with a carboxylic acid chloride, to give a triphenylester of the formula

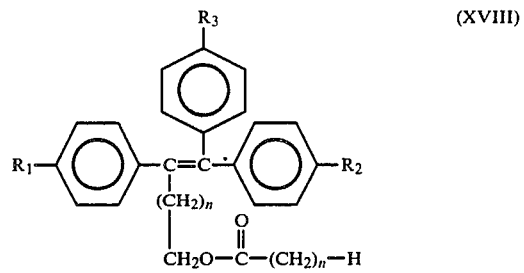

(XVIII)

wherein $R_1$, $R_2$, $R_3$ and n are as defined before. Then the ester group is hydrolysed to give the triphenylalkenol (XI). Reacting the triphenyldiol (IX), the triphenylcyclo-oxa-alkane (X) or the protected or unprotected triphenyldiol (VIII), wherein $OR_8$ is a mixed acetal, benzyloxy or hydroxy, with an appropriate acid catalyst in a carboxylic acid containing 1 to 5 carbon atoms gives likewise the triphenylester (XVIII). Stronger reaction conditions simultaneously break a possible ether bond thus giving the corresponding phenol. The triphenylester (XVIII) can also be obtained for example by refluxing or warming the triphenylalkenol (XI) in a carboxylic acid of 1 to 5 carbon atoms.

Yet another process for the preparation of the compounds of the invention comprises dealkylation of an ether of the formula

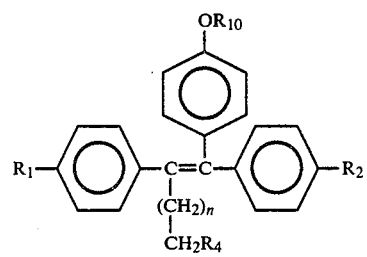

(XIX)

wherein $R_1$, $R_2$, $R_4$ and n are as defined before and $R_{10}$ is an alkyl or aralkyl group, to give the corresponding phenol or 4-hydroxyphenyl-diphenylalkene of the formula

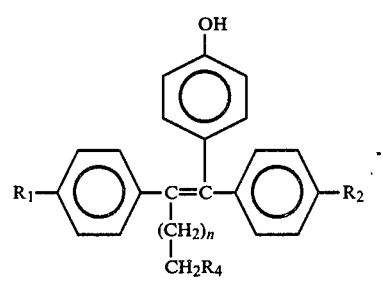

(XX)

wherein $R_1$, $R_2$, $R_4$ and n are as defined before. In the same way the cleavage of ether bonds from the other two phenyl groups can be performed. Furthermore several ether bonds can simultaneously be broken to give bis- or trisphenols.

Yet another process for the preparation of the compounds of the invention comprises alkylation of the 4-hydroxyphenyl-diphenylalkene (XX) for example either with diazomethane or in alkaline conditions with an alkylhalide derivative of the formula

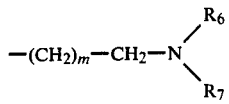  (XXI)

wherein $R_{11}$ is an alkyl group of 1 to 4 carbon atoms, benzyl, methoxymethyl, 2,3-dihydroxypropyl or

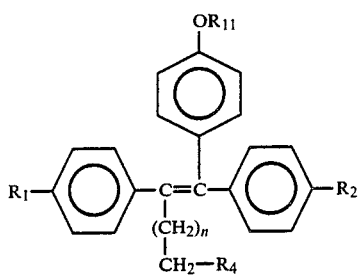

wherein $R_6$, $R_7$ and m are as defined before, to give a triphenylalkene-ether of the formula

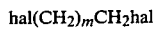  (XXII)

wherein $R_1$, $R_2$, $R_4$, $R_{11}$ and n are as defined before. Simultaneously one or more phenolic OH-groups can be alkylated to give mono-, bis- or tris-ethers. The 4-hydroxyphenyl-diphenylalkene (XX) can also be alkylated with a dihaloalkene of the formula hal(CH$_2$)$_m$CH$_2$hal  (XXIII)

wherein m is as defined before and hal are halogen atoms, which can be the same or different. This gives a 4-(haloalkoxy)phenyl-diphenylalkene of the formula

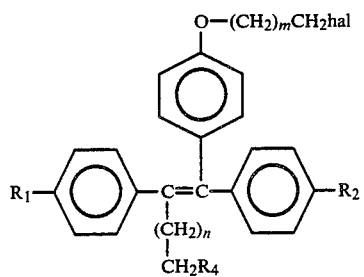  (XXIV)

wherein $R_1$, $R_2$, $R_4$, n, m and hal are as defined before. This compound is reacted with an amine of the formula

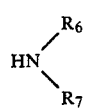  (XXV)

wherein $R_6$ and $R_7$ are as defined before, to give a (4-aminoalkoxy)phenyl-diphenylalkene of the formula

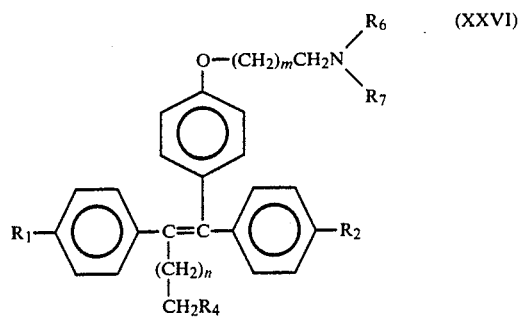  (XXVI)

wherein $R_1$, $R_2$, $R_4$, $R_6$, $R_7$, m and n are as defined before.

The preparation of the saturated phenols corresponding formula (II) by dealkylating and the alkylations of them can be performed in the same way as described above for the unsaturated phenols corresponding to formula (I) (see formulae XIX–XXVI).

Another method for the preparation of the compounds of the invention comprises converting the triphenylalkenol (XI) by various methods into a triphenyl-halide of the formula

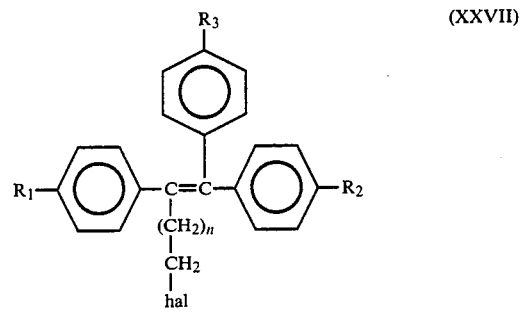  (XXVII)

or by reacting it with, for example, sulfonic acid chloride to give the corresponding triphenylsulfonate of the formula

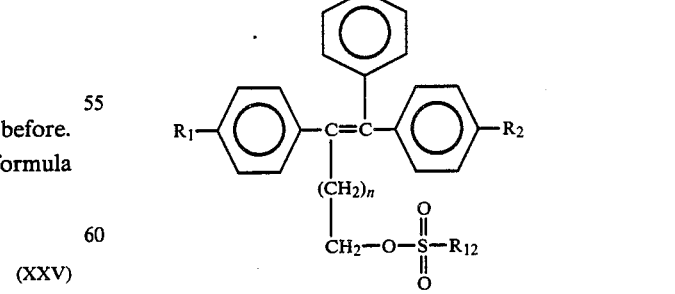  (XXVIII)

wherein $R_1$, $R_2$, $R_3$ and n are as defined before, hal is halogen and $R_{12}$ is methyl or 4-tolyl. Accordingly, the triphenyldiol (IX) can be converted either to a triphenylhydroxyhalide of the formula

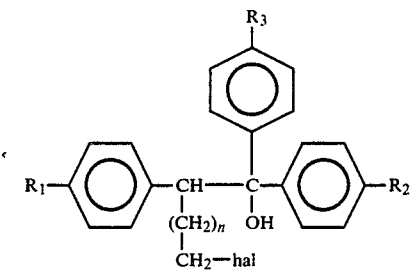

(XXIX)

or to a triphenylhydroxysulfonate of the formula

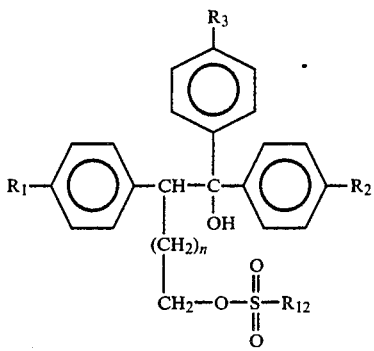

(XXX)

wherein $R_1$, $R_2$, $R_3$, $R_{12}$, n and hal are as defined before. Dehydration of the triphenylhydroxyhalide (XXIX) and the triphenylhydroxysulfonate (XXX) gives the corresponding triphenylhalide (XXVII) and triphenylsulfonate (XXVIII). Furthermore, the triphenylhalide (XXVII) can also be obtained in one single reaction step from the triphenyldiol (IX) as well as from the triphenylcyclo-oxa-alkane (X). For example by treating the triphenyldiol (IX) with thionyl chloride the triphenylchloride (XXVII, hal=Cl) is obtained. The halides (XXVII) can also be prepared from the corresponding sulfonates (XXVIII) or from other halides (XXVII).

Desoxybenzoin or a desoxybenzoin derivative (III) can be alkylated also with a dihaloalkane of the formula

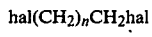 (XXXI)

wherein n is as defined before and hal are halogen atoms, which can be the same or different, to give a diphenyloxohalide of the formula

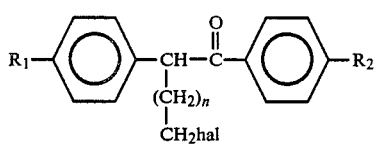

(XXXII)

wherein $R_1$ and $R_2$ are as defined before or mixed acetal, hal and n are as above. In a further reaction the diphenyloxohalide (XXXII) is reacted with a phenylmagnesiumhalide derivative (VI) or with a corresponding lithium compound (VII). This reaction gives a triphenylhydroxyhalide (XXIX), wherein $R_1$, $R_2$ and $R_3$ are as defined before or mixed acetal, hal and n are as above. The same diphenylhydroxyhalide is obtained by interchange of the groups $R_2$ and $R_3$ of the intermediate and reagent. The removal of the possible mixed acetal protecting group from the phenyl ring gives the triphenylhydroxyhalide (XXIX). By combining the removal of the possible protecting group and the dehydration the triphenylhalide (XXVII) can be obtained in one single step from triphenylhydroxyhalide (XXIX), wherein $R_1$, $R_2$ and $R_3$ are as defined before or mixed acetal, hal and n are as defined above.

Yet another method for the preparation of the compounds of the invention comprises converting a triphenylhalide of the formula

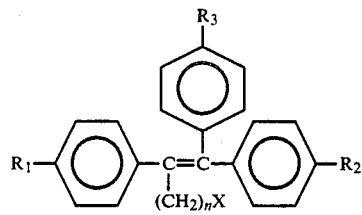

(XXXIII)

wherein $R_1$, $R_2$, $R_3$ and n are as defined before, and X is halogen, to the corresponding Grignard-complex or lithium salt (XXXIII) wherein X is Mghal or Li, respectively. Reacting this complex or salt with formaldehyde, ethylene oxide or trimethylene oxide gives a triphenylalkenol (XI) wherein n is 1 to 4.

Reacting a triphenylhalide (XXVII) or a triphenylsulfonate (XXVIII) wherein n is 0 to 3, with a cyano group gives a triphenyl nitrile of the formula

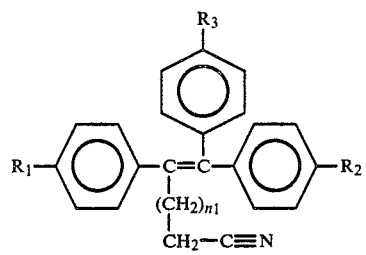

(XXXIV)

wherein $R_1$, $R_2$, $R_3$ and $n_1$ are as defined before. Hydrolysis of this compound gives the corresponding triphenylcarboxylic acid of the formula

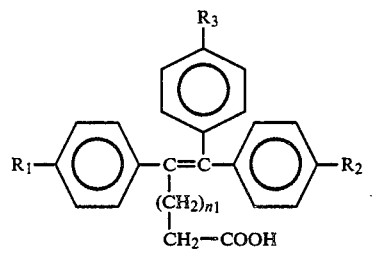

(XXXV)

wherein $R_1$, $R_2$, $R_3$ and $n_1$ are as above. The triphenylcarboxylic acid (XXXV) can be reduced either in one step or for example via an ester intermediate to give a triphenylalkenol (XI) wherein n is 1-4.

According to another method the Grignard-complex or the lithium salt (XXXIII) is reacted with carbon dioxide to give a triphenylcarboxylic acid of the formula

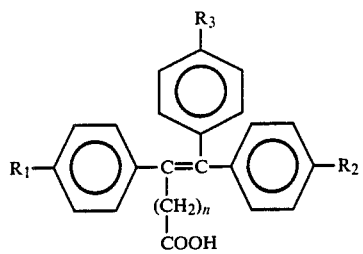

(XXXVI)

wherein $R_1$, $R_2$, $R_3$ and n are as above. The compound (XXXVI) is reduced to the triphenylalkenol (XI) as described before.

Another method for the preparation of the compounds of the invention is the alkylation of desoxybenzoin derivative (III), with an alkylating agent consisting of an acetal- or mixed acetal-protected haloaldehyde of the formula

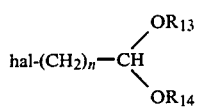

(XXXVII)

wherein n is as above and $R_{13}$ and $R_{14}$, which can be the same or different, are for example alkyl groups which may be linked, e.g. ethyl groups which may form together a propylene bridge of a 1,3-dioxolane ring. The reaction product obtained is a protected diphenyloxoaldehyde of the formula

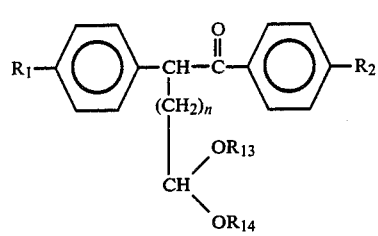

(XXXVIII)

wherein $R_1$ and $R_2$ are as before or mixed acetal, and $R_{13}$, $R_{14}$ and n are as above. The compound (XXXVIII) is then reacted with a phenylmagnesiumhalide (VI) or the corresponding lithium compound (VII). The reaction gives a protected triphenylhydroxyaldehyde of the formula

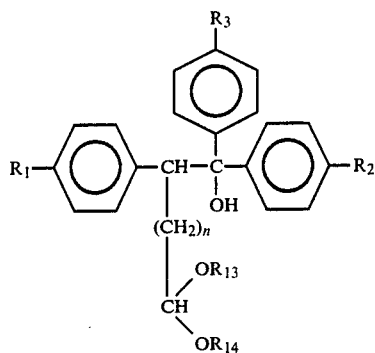

(XXXIX)

wherein $R_1$, $R_2$ and $R_3$ are as before or mixed acetal and $R_{13}$, $R_{14}$ and n are as above.

By interchange of the groups $R_2$ and $R_3$ of the intermediate (XXXVIII) and the reagents (VI) or (VII), the same protected triphenylhydroxyaldehyde (XXXIX) is obtained. The protecting group can be removed for example by an appropriate acid catalyst in the presence of water. In the same step a possible mixed acetal protecting group attached to the phenyl ring will be removed. This results, depending on the value of n, either in a triphenylhydroxyaldehyde (XXXXa), the corresponding cyclic hemiacetal (XXXXb), or in a mixture thereof

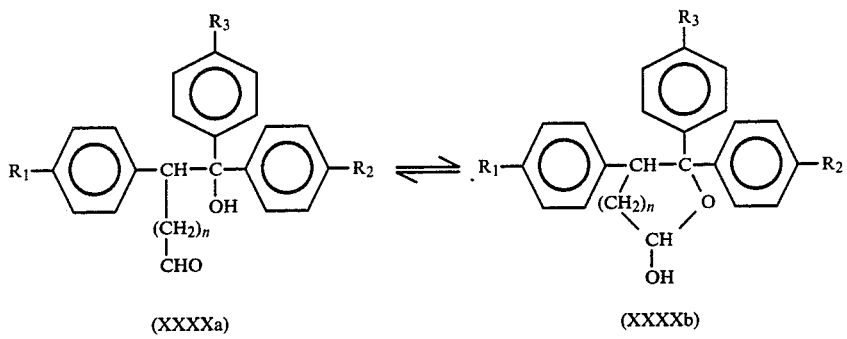

wherein $R_1$, $R_2$, $R_3$ and n are as defined before.

Dehydration of the compound (XXXXa) or the corresponding compound (XXXXb) or a mixture thereof results in a triphenylaldehyde of the formula

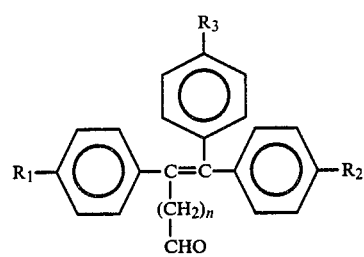

(XXXXI)

wherein $R_1$, $R_2$, $R_3$ and n are as defined before. On the other hand, dehydration of a protected triphenylhydroxyaldehyde (XXXIX) results in a protected triphenylaldehyde of the formula

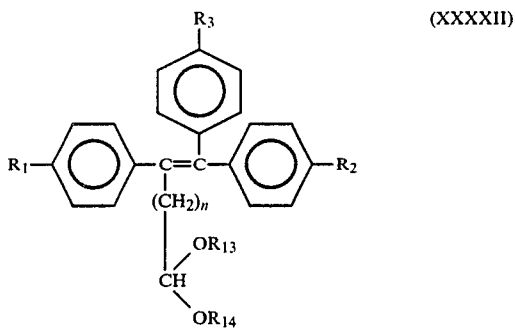

(XXXXII)

wherein $R_1$, $R_2$ and $R_3$ are as defined before or mixed acetal, and $R_{13}$, $R_{14}$ and n are as above. The protecting group is removed as above, after which the triphenylaldehyde (XXXXI) is obtained. The triphenylaldehyde (XXXXI) can further be obtained by oxidation of the triphenylalkenol (XI) or by reduction of the triphenylcarboxylic acid (XXXVI), either in a single step or via an intermediate.

The triphenylaldehyde (XXXXI) can be dealkylated and alkylated in the same way as the alcohols (see formulae XIX–XXVI) as described before.

The triphenylalkane compounds of the invention can be prepared by catalytic hydrogenation of the triphenylalkene derivative (I) wherein $R_1$, $R_2$, $R_3$, $R_4$ and n are as defined before, or a triphenylalkane derivative (II), wherein $R_1$, $R_2$, $R_3$, $R_4$, $R_5$ and n are as defined before except that $R_5$ is other than hydrogen, to give the corresponding triphenylalkane derivative of the formula

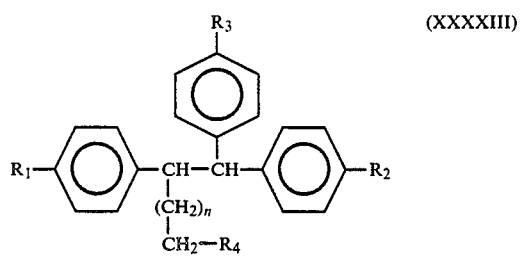

(XXXXIII)

wherein $R_1$, $R_2$, $R_3$, $R_4$ and n are as defined before. The triphenylalkane derivatives (XXXXIII) can be converted in the same way as the corresponding triphenylalkene derivatives as described before. Such conversion reactions are for example dealkylation of the phenyl ethers, alkylation of the phenols, preparation of halides and sulfonates, extension of the side chain, and reduction and oxidation reactions.

When the product is a compound of formula I or another triphenylalkene derivative containing a double bond, a mixture of the (Z)- and (E)-isomers is obtained. By choice of appropriate reaction conditions, an isomer mixture enriched in respect of one or the other of the isomers can be obtained. The reaction conditions can also be chosen so that equal amounts of the isomers are formed.

For example, when a protected diphenyloxoalkanol (V) is reacted by a Grignard reaction with a phenylmagnesiumhalide derivative (VI) either the (RR,SS)- or the (RS,SR)-enantiomer pair is obtained, due to asymmetrical induction. Interchanging $R_2$ and $R_3$ between the starting material and the reagent results in the opposite enantiomer pair.

Reacting the aluminium complex of formula (XIV) with the benzophenone derivative (XV) gives equal amounts of the (RR,SS)- and (RS,SR)-triphenyldiol (IX).

The preparation of triphenylcyclo-oxa-alkanes from triphenyldiols (IX) gives almost only the (RR,SS)-pair starting from the (RR,SS)-pair, and a mixture of the (RS,SR)- and (RR,SS)-pairs starting from the (RS,SR)-pair.

The preparation of the triphenylalkane derivative (II), wherein $R_5$ is H, from the triphenylalkene derivative (I) by catalytic hydrogenation gives the (RR,SS)-enantiomer pair from the (Z)-isomer and the (RS,SR)-enantiomer pair from the (E)-isomer.

The alkylation of phenols generally gives the pure isomer or enantiomer pair from the corresponding pure isomer or enantiomer pair, although some isomerisation may occur depending on the conditions used. A mixture of starting materials naturally results in a corresponding mixture of products.

Conversion of the functional group at the end of the alkane or the alkene chain gives in most cases the pure isomer or enantiomer pair from the corresponding pure isomer or enantiomer pair. Mixtures give of course the corresponding mixtures.

The pure (Z)- and (E)-isomers as well as the pure (RR,SS)- and (RS,SR)-enantiomer pairs can be isolated from a mixture of the isomers either by fractional crystallization, fractional dissolution, chromatographically or by a combination thereof. The pure (Z)- and (E)-isomers of the amines as well as the (RR,SS)- and (RS,SR)-enantiomer pairs can be isolated from the mixture of the isomers both when the compounds are free bases and when they are in salt form.

Accordingly the isomers and enantiomers of the phenols can be isolated both when the phenols are free "acids" and when they are in the salt form.

The salts of the amines are prepared by reacting the amines with organic or inorganic acids, for example citric acid or hydrochloric acid.

The quaternary ammonium salts are obtained by reacting the amines with alkylating agents, for example methyl iodide or benzyl chloride. The N-oxides are prepared by reacting the amines with a suitable oxidizing agent, for example hydrogen peroxide.

The salts of the phenols are obtained by reacting the phenols with inorganic bases, for example sodium hydroxide. Furthermore, esters of the phenols are obtained by reacting the phenols with an aliphatic or aromatic carboxylic acid, the corresponding acid chloride or acid anhydride.

As stated herein above, the compounds of the general formula (I) and (II) and their non-toxic, pharmaceutically acceptable salts, esters and N-oxides exhibit valuable pharmacological properties in particular hormonal properties as oestrogenic and anti-oestrogenic agents (depending upon dosage used). They also have progestanic and anti-tumor activity, in particular against hormone-dependent, and especially oestrogen-dependent, tumours.

Administration of the compounds of formula (I) and (II), their non-toxic, pharmaceutically acceptable salts or esters or mixtures thereof may be achieved parenterally, intravenously or orally. Typically, an effective amount of the derivative is combined with a suitable pharmaceutical carrier. As used herein, the term "effective amount" encompasses those amounts which yield the desired activity without causing adverse side-effects. The precise amount employed in a particular situation is dependent upon numerous factors such as method of administration, type and size of mammal, condition for which the derivative is administered, etc., and of course the structure of the derivative.

The pharmaceutical carriers which are typically employed with the compounds of the present invention may be solid or liquid and are generally selected with the planned route of administration in mind. Thus, for example, solid carriers include lactose, sucrose, gelatin and agar, while liquid carriers include water, syrup, peanut oil and olive oil. Other suitable carriers are well-known to those skilled in the art of pharmaceutical formulations. The combination of the derivative and the carrier may be fashioned into numerous acceptable forms, such as tablets, capsules, suppositories, solutions, emulsions, and powders.

The affinity of the new compounds for oestrogen receptors was determined by the ability to compete with $^3$H-labelled 17-$\beta$-estradiol in rat uterus cytosol preparation. After incubation, receptor-bound and receptor-unbound ligands were separated by a known dextrancharcoal method. (Korenman, S. G.: "Comparative binding affinity of estrogens and its relation to oestrogenic potency". Steroids 13: 163–177, 1969).

The oestrogen-antiestrogen (progesterone) effect of the new compounds in vivo was determined as follows: (1) The oestrogenic properties were determined by administering the new compounds, suspended in sesame oil, subcutaneously to 21 days old immature mice on three consecutive days. The mice were killed on the fourth day and the uterus was weighed. Estradiol (positive control) increases the weight of the uterus. The weight correlates with the oestrogenic effect of the compound tested. (2) The antiestrogenic effects of the new compounds were determined in a similar manner in immature mice. In this case, the ability of the molecules to inhibit oestrogen-induced uterus weight increase was also investigated.

The progestanic effects of the new compounds were studied in a similar manner to the oestrogenic effects. Medroxy-progesterone acetate, which decreases uterus weight, was used as reference.

The anti-tumour effect was studied in vitro as follows:

The growth of MCF-7 cell line (human mammary adenocarcinoma, known to be oestrogen-dependent) was evaluated in the presence or absence of estradiol, medroxyprogesterone acetate or the compound to be investigated. Combinations of compound under test plus estradiol or medroxyprogesterone were also studied. The amount of living cells after 4 h, 24 h and 48 h incubations were determined by bioluminescence assay (intracellular ATP determination).

The anti-tumour effect was investigated in vivo against DMBA-induced rat mammary adenocarcinomas, transplantable mammary and ovarial adenocarcinoma and transplantable prostatic squamous cell carcinoma by the following methods:

Mammary adenocarcinomas were induced by DMBA in 35–40 days old female rats. Treatment with the compound under test was started after palpable tumours had appeared. Tumour size and numbers of tumours were evaluated twice a week. Tumour sizes in the control group, treated with solvent, were compared with the test groups.

The activity of the molecules against other tumours was studied by administering the molecules by stomach tube to animals implanted with transplantable uterus sarcoma (mice) or prostatic adenocarcinoma (rats).

Daily or twice weekly administration schedules were employed. NMRI mice (about 20 g, females) and Fischer 344 rats (about 200 g, males) were used. Estramustine phosphate served as positive control.

Transplantable rat mammary adenocarcinoma was developed by inoculating pieces of DMBA-induced carcinomas subcutaneously to healty mature female rats. A tumour which expressed malignant growth was selected for further transplantations. Other transplantable tumours were inoculated subcutaneously as washed cell suspension ($10^7$ cells/animal).

The compounds of the invention possessed good affinities to estrogen receptors as measured by the dextran-charcoal method. The results are shown in table 1 as follows:

TABLE 1

| affinity | concentration of compound where 50% competition (inhibition) with $^3$H—estradiol occurred |
|---|---|
| +++ | $10^{-6}$ M (inhibition)-$10^{-7}$ M (weak affinity) |
| ++ | $10^{-5}$ M (inhibition)-$10^{-6}$ M (weak affinity) |
| + | $10^{-4}$ M (inhibition)-$10^{-5}$ M (weak affinity) |
| ± | $10^{-4}$ M no clear inhibition |

Estrogen receptor affinities of certain compounds of formulae (I) and (II)

| No. | Investigated compound Name | Affinity |
|---|---|---|
| 1. | 1,2-diphenyl-1-(4-hydroxyphenyl)-butane-1,4-diol, (RR,SS)—enantiomer pair | ++ |
| 2. | 2,3-diphenyl-2-(4-hydroxyphenyl)tetrahydrofuran, (RR,SS)—enantiomer pair | +++ |
| 3. | 1,2-diphenyl-1-(4-methoxyphenyl)-1-buten-4-ol | ++ |
| 4. | 1,2-diphenyl-1-[4-[2-(N,N—dimethylamino)ethoxy]phenyl]-1-buten-4-ol, (Z)—isomer | ++ |
| 5. | 2,3-diphenyl-2-(4-hydroxylphenyl)tetrahydropyran (RR,SS)—enantiomer pair | +++ |
| 6. | 1,2-diphenyl-1-(4-hydroxphenyl)-1-penten-5-ol (Z,E)—isomers | ++(+) |
| 7. | 4-chloro-1,2-diphenyl-1-[4-[2-(N,N—dimethylamino)ethoxy]phenyl]-1-butene, (Z)—isomer | +++ |
| 8. | 1-phenyl-1,2-bis(4-hydroxyphenyl)-butane-1,4-diol | ++ |
| 9. | 2-phenyl-2,3-bis(4-hydroxyphenyl)tetrahydrofuran | +++ |
| 10. | 1,2-diphenyl-1-(4-hydroxyphenyl)-1-buten-4-ol, (E)—isomer | +++ |
| 11. | 1,2-diphenyl-1-(4-hydroxyphenyl)-1-buten-4-ol (Z)—isomer | ++ |
| 12. | 1,2-diphenyl-1-[4-[2-(N,N—dimethylamino)ethoxy]phenyl]-1-buten-4-ol (E)—isomer | + |
| 13. | 4-bromo-1,2-diphenyl-1-[4-[2-(N,N—dimethylamino)ethoxy]phenyl]-1-butene (Z)—isomer | +++ |
| 14. | 4-chloro-1,2-diphenyl-1-(4-hydroxyphenyl)-butane (RR,SS)—enantiomer pair | +++ |
| 15. | 4-chloro-1,2-diphenyl-1-(4-hydroxyphenyl)-1-butene (Z)—isomer | ++ |
| 16. | 2,3-diphenyl-2-[4-[2-(N,N—dimethylamino)ethoxy]phenyl]-tetrahydrofuran (RR,SS)—enantiomer pair | + |
| 17. | 1,2-diphenyl-1-[4-[2-(N,N—dimethylamino)ethoxy]phenyl]butane-1,4-diol (RR,SS)—enantiomer pair | + |
| 18. | 4-chloro-1,2-diphenyl-1-[4-[2-(N,N—dimethylamino)ethoxy]phenyl]-1-butene (E)—isomer | + |

The estrogenic effect of compounds of formula (I) and (II) as measured by their ability to increase the weight of immature mouse uterus was always far less than that of estradiol, the positive control. The estrogenic effect of the compounds 5, 7, 13 and 14 could be seen only at the higher concentrations investigated. At the dose of 5 mg/kg the effect of the first was 41% less than that of estradiol 0.05 mg/kg. The corresponding values for the latter compounds were about 50%. The compounds 4 and 11 and compounds 2, 16 and 17 possessed no estrogenic effects of their own up to doses of 5 mg/kg.

The compounds 4, 7 and 11, 13, 14 and 15 possessed anti-estrogenic effects as measured by their ability to inhibit estradiol induced weight increase in immature mouse uterus. Compounds 4 and 7 caused at the dose of 0.5 mg/kg, and compounds 11, 13, 15 and 14 at the dose of 5 mg/kg, a 12%, 27%, 31%, 25%, 25% and 20% inhibition of estradiol induced effect in mouse uterus respectively.

The progestanic effects of the compounds were measured as described earlier. Medroxyprogesterone acetate, the positive control, caused up to 40% inhibition in the weight of immature mouse uterus. The effects of compound 2 could purely be considered to be due to its progestanic effect. It had no antiestrogenic or estrogenic effect of its own up to 5 mg/kg. At the dose of 0.05 mg/kg the weight of mouse uterus was decreased by 50% and a synergistic effect with medroxyprogesterone was seen.

The compounds 4 and 11 given alone could cause a 38% and 56% reduction respectively in the weight of mouse uterus, an effect which could in part be considered to be due to their antiestrogenic effects. Compound 11 was found to possess a synergistic effect with medroxyprogesterone and compound 4 caused a slight inhibition, yet a 17% reduction in the weight of uterus was seen. Compound 5 of formula (II) had no antiestrogenic effect and could decrease the weight of uterus by 34% (0.05 mg/kg) due to its progestanic effect. No inhibition of medroxyprogesterone was seen at that dose. With increased doses, however, a weak estrogenic effect could be seen which effect overcame that of medroxyprogesterone. A slight increase in the weight of uterus was achieved. Compound 7 besides possessing antiestrogenic and estrogenic properties was found to be progestanic and cause slight inhibition of medroxyprogesterone at the lowest dose studied.

In tables 2A and 2B a summary of the estrogenic/antiestrogenic and progestanic effect can be seen. The percentages refer to increase/reduction in the weights of mice uterus.

The antitumour effects of compounds of formula (I) and (II) have been tested in vitro against MCF-7 human mammary adenocarcinoma cell line and in vivo against DMBA-induced rat mammary adenocarcinomas, rat ovarial carcinoma, rat prostatic carcinoma and mouse uterus sarcoma.

On table 3 the antitumour effects of certain compounds of formula (I) and (II) can be seen. The results are shown as follows:

| effect | $IC_{50}$ = concentration of compound where 50% inhibition of cell growth could be seen. |
|---|---|
| +++ | $10^{-6} - 5 \times 10^{-6}$ M |
| ++ | $5 \times 10^{-6} - 10^{-5}$ M |
| + | $10^{-5} - 5 \times 10^{-5}$ M |
| − | $5 \times 10^{-5}$ M |

TABLE 2

Summary of estrogenic/antiestrogenic and progestanic effects of compounds of formula (I) and (II)

| Given | 2 | 4 | 5 | 7 | 11 |
|---|---|---|---|---|---|
| alone | progestanic 50% reduction | anti-estrogenic progestanic 31% reduction | progestanic 34% reduction | estrogenic progestanic | anti-estrogenic 56% reduction |
| with estradiol 0.05 mg/kg | no synergism or inhibition | anti-estrogenic 21% reduction | no synergism or inhibition | anti-estrogenic 27% reduction | anti-estrogenic 31% reduction |
| with medroxy-progesterone 0.06 mg/kg | synergistic effect 53% reduction compared to control | weak inhibition 17% reduction compared to control | no inhibition 34% reduction | weak inhibition 14% reduction compared to control | no inhibition 40% reduction |

| Given | 14 | 15 | 9 | 13 | 18 |
|---|---|---|---|---|---|
| alone | estrogenic 50% increase | estrogenic 20% increase | estrogenic 50% increase | estrogenic 50% increase | estrogenic 20% increase |
| with estradiol 0.05 mg/kg | anti-estrogenic 20% reduction | anti-estrogenic 25% reduction | not anti-estrogenic <10% reduction | anti-estrogenic 25% reduction | not anti-estrogenic <10% reduction |
| with medroxy-progestrone 0.06 mg/kg | not tested | not tested | not tested | weak inhibition 14% reduction compared to control | no effect |

TABLE 3

The antitumour effect of certain compounds of formula (I) and (II) against MCF-7 cell line.

| Investigated Compound | Antitumour effect |
|---|---|
| 4 | +++ |
| 5 | +++ |
| 7 | +++ |
| 12 | +++ |
| 13 | +++ |
| 18 | +++ |
| 2 | ++ |
| 14 | ++ |
| 15 | ++ |
| 16 | ++ |
| 6, (E)—isomer | ++ |

As can be seen the compounds tested were very effective in vitro against MCF-7 mammary cells and by increasing the concentration the death of the cell line was achieved with every compound.

The antitumour effect in vivo of compounds 4 and 7 has been tested against DMBA-induced rat mammary adenocarcinoma. At the dose 10 mg/kg of compound 4 the growth rate of tumours was slowed to one eighth compared to that of the controls. The antitumour effect of compound 7 had been found at the dose range of 1.0–30 mg/kg. At the highest dose used the growth of the tumours was found to stop (table 4).

TABLE 4

The size and growth of DMBA induced tumours during treatment with compound 7 compared with the control group.

| Day of treatment | Control size of tumour | growth | Compound 7 30 mg/kg size of tumour | growth |
| --- | --- | --- | --- | --- |
| 1. | 3.914 | 0 | 1.5188 | 0 |
| 3. | 4.716 | 0.803 | 1.6739 | 0.1551 |
| 7. | 8.509 | 4.596 | 1.3070 | −0.2118 |
| 9. | 11.622 | 7.708 | 1.0474 | −0.4714 |
| 14. | 16.176 | 12.262 | 1.0179 | −0.5392 |
| 17. | 17.473 | 12.826 | 0.0820 | −0.5752 |
| 21. | 22.695 | 18.049 | 0.0721 | −0.5851 |
| 25. | 29.542 | 24.896 | 0.0891 | −0.5682 |
| 28. | 35.115 | 30.469 | 0.09316 | −0.5640 |
| 35. | 32.803 | 28.156 | 0.1193 | −0.5379 |

The size refers to the width x height of the tumour. The growth rate is a difference between sizes compared with that of the first day of the treatment. Antitumour effect less than that of compound 7 against DMBA-induced mammary cancer was observed with the compounds 2, 12 and 13.

The effect of compound 7 against rat ovarial carcinoma and mouse uterus sarcoma had been tested against transplantable tumours using methods described earlier. After two weeks' treatment with 100 mg/kg, the size of the uterus sarcoma was 30% smaller than that of control and after ten days' treatment with 5 mg/kg, the size of rat ovarial carcinoma was 20% smaller compared with the control.

The effect of compound 2 against transplantable prostatic carcinoma was measured as described earlier. The size of the tumour after 12 days' treatment with compound 2 (1 mg/kg) was 29% smaller than that of the control.

Acute toxicity. $LD_{50}$ p.o. in mice, varies from 1000 to 3200 mg/kg for the compounds tested. The clinical dosage ranges for oral administration may vary from 10 to 200 mg per day for an adult person.

The following Examples illustrate the invention.

The $^1$H NMR spectra were measured in on a Perkin-Elmer R 24A or a Bruker WP 80 DS instrument using TMS as internal reference (Chemical shifts in $\delta$, ppm). The letters s, d, t and m are used to indicate a singlet, doublet, triplet or multiplet, respectively. In the same connection, the number of hydrogen atoms is also stated. Masspectra were recorded by kratos MS 80 RF using direct inlet and 70 ev ionization voltage.

EXAMPLE 1

(a) 4-[(tetrahydropyran-2-yl)oxy]-1,2-diphenylbutan-1-one

A mixture containing 19.6 g of desoxybenzoin, 20.9 g of tetrahydropyran-2-yl ether-protected bromoethanol, 1.0 g of TEBAC and 50 ml of 48% sodium hydroxide solution is stirred for 2 h at 75° C. Water is added and the product extracted in toluene. The toluene solution is washed with water and dried over sodium sulfate. Finally the solvent is evaporated. The yield is quantitative, but the oily product contains about 20% O-alkylation product.

(b) 4-[(tetrahydropyran-2-yl)oxy]-1,1,2-triphenylbutan-1-ol.

First a Grignard complex is prepared under dry conditions by allowing 3.6 g of magnesium turnings in 25 ml of dry tetrahydrofuran to react with 23.6 g of bromobenzene in 50 ml of dry tetrahydrofuran. Then the evaporation residue obtained in step (a) in 75 ml of dry tetrahydrofuran is added. The reaction mixture is refluxed for 2 h. The cooled mixture is poured into a saturated solution of ammonium chloride. After shaking, the organic layer is separated. The extraction is repeated with ether. Then the organic layers are combined and dried over sodium sulfate. Finally the solvent is evaporated.

(c) 1,1,2-triphenylbutane-1,4-diol

The evaporation residue obtained in step (b) is dissolved in a mixture containing 400 ml of absolute ethanol, 10 g of concentrated sulfuric acid and 75 ml of water. The mixture is stirred for 2 h at room temperature. The solution is neutralized with 2M sodium hydroxide solution, after which the ethanol is evaporated. Water is added to the residue. Then the product is extracted in ethyl acetate. The ethyl acetate solution is dried over sodium sulfate, and the solvent is evaporated. The product is recrystallized from toluene. The yield is 16.5 g (52% from desoxybenzoin) and m.p. 185°–7° C.

$^1$H-NMR-spectrum (CD$_3$OD): $\delta$2.06 (2H, q), 3.33 (2H, t), 3.92 (1H, t), 4.76 (2H, s), 6.85–7.45 (13H, m), 7.68 (2H, dd).

EXAMPLE 2

2,2,3-triphenyltetrahydrofuran 31.8 g of 1,1,2-triphenylbutane-1,4-diol obtained as described in Example 1(c) are dissolved in a mixture containing 400 ml of absolute ethanol, 10 ml of concentrated sulfuric acid and 75 ml of water. Then the mixture is stirred for 3 h at 45° C. The solution is neutralized with 2M sodium hydroxide solution, after which the ethanol is evaporated. Water is added into the residue and the product is extracted in toluene. The toluene solution is dried over sodium sulfate, and the solvent is evaporated. Recrystallization is performed from ethanol. The yield of the product is 26.4 g (88%) and m.p. 112.°–3° C.

$^1$H-NMR-spectrum (CDCl$_3$): $\delta$1.90–2.60 (2H, m), 3.85–4.55 (3H, m), 6.90–7.45 (13H, m), 7.63 (2H, dd).

EXAMPLE 3

(a) 4-acetoxy-1,1,2-triphenyl-1-butene 30.0 g of 2,2,3-triphenyltetrahydrofuran are dissolved in 125 ml of acetic acid, after which 25 ml of 40% hydrogen-bromide in acetic acid are added. The mixture is stirred for 1 h at 75° C. The solvent is evaporated, and 1M sodium carbonate solution is added in excess. The product is extracted in toluene. The toluene solution is dried over sodium sulfate and the solvent is evaporated. The product is recrystallized from aqueous methanol and then has m.p. 81°–3° C. The yield is 28.7 g (84%).

¹H-NMR-spectrum (CDCl₃): δ1.82 (3H, s), 2.78 (2H, t), 4.02 (2H, t), 6.85 (5H, s), 7.02 (5H, s), 7.21 (5H, s). MS: m/z 342 (M+, 5), 282 (64), 205 (28), 191 (100), 167 (27), 91 (70).

(b) 1,1,2-triphenyl-1-buten-4-ol 34.2 g of 4-acetoxy-1,1,2-triphenyl-1-butene are dissolved in 200 ml of 94% ethanol, after which 20 ml of water and 45 ml of a 20% sodium hydroxide solution are added. The mixture is refluxed for 1 h. The solution is neutralized with 2M hydrochloric acid, after which the ethanol is evaporated. Water is added into the residue. The product is extracted in ethyl acetate, the ethyl acetate solution is dried over sodium sulfate and the solvent is evaporated. The product is recrystallized from a mixture of water and methanol and then has m.p. 117°–9° C. The yield is 23.7 g (79%).

¹H-NMR-spectrum (CDCl₃): δ1.34 (1H, s), 2.73 (2H, t), 3.05 (2H, t), 6.90 (5H, s), 7.11 (5H, s), 7.25 (5H, s).

(c) 4-tosyloxy-1,1,2-triphenyl-1-butene

The reaction is performed under dry conditions. 30.0 g of 1,1,2-triphenyl-1-butene-4-ol are dissolved in 100 ml of dry pyridine. Then with stirring and cooling the mixture on ice, 57.0 g of 4-toluenesulfonic acid chloride in 50 ml of dry pyridine are added dropwise to the mixture. The mixture is stirred for 6 h at 0° C. Then 250 ml of ice-cold water and 750 ml of cold 2M hydrochloric acid are added. The precipitate is collected by filtration and washed with water. Finally the product is recrystallized from ethanol. The yield is 36.8 g (81%) of a product having m.p. 137°–9° C.

¹H-NMR-spectrum (CDCl₃): δ2.32 (3H, s), 2.77 (2H, t), 3.92 (2H, t), 6.86 (5H, s), 6.98 (5H, s), 7.16 (2H, d), 7.21 (5H, s), 7.60 (2H, d).

EXAMPLE 4

(a)
4-[(tetrahydropyran-2-yl)oxy]-2-phenyl-1-(4-methoxyphenyl)butan-1-one

The compound is prepared from 22.6 g of 4-methoxydesoxybenzoin and 20.9 g of tetrahydropyran-2-yl ether-protected bromoethanol according to the procedure described in Example 1(a).

(b)
4-[(tetrahydropyran-2-yl)oxy]-1,2-diphenyl-1-(4-methoxyphenyl)butan-1-ol (RR,SS and RS,SR)

The (RR,SS)-isomers are prepared from the evaporation residue obtained in step (a) and 28.1 g of 4-bromoanisole using the procedure described in Example 1(b).

The (RS,SR)-isomers are prepared from the evaporation residue obtained in step (a) and 23.6 g of bromobenzene in the same manner as (RR,SS)-isomers above.

(c) 1,2-diphenyl-1-(4-methoxyphenyl)butane-1,4-diol (RR,SS and RS,SR)

The (RS,SS)-isomers are prepared from the evaporation residue of (RR,SS)-isomers obtained in step (b) according to the procedure described in Example 1(c). The product is recrystallized from toluene. The yield is 13.9 g (40% from desoxybenzoin) and the product has m.p. 124°–6° C.

¹H-NMR-spectrum (CD₃OD): δ2.06, (2H, q), 3.32 (2H, t), 3.77 (3H, s), 3.84 (1H, dd), 4.78 (2H, s), 6.80–7.25 (12H, m), 7.56 (2H, d).

The (RS,SR)-isomers are prepared from the evaporation residue of (RS,SR)-isomers obtained in step (b) in the same manner as the (RR,SS)-isomers above. The product is recrystallized from toluene. The yield is 16.0 g (46% from 4-methoxydesoxybenzoin) and the m.p. of the product is 172°–4° C.

¹H-NMR-spectrum (CD₃OD): δ2.03 (2H, q), 3.32 (2H, t), 3.63 (3H, s), 3.86 (1H, t), 4.75 (2H, s), 6.54 (2H, d), 6.95–7.45 (10H, m), 7.65 (2H, dd).

EXAMPLE 5

2,3-diphenyl-2-(4-methoxyphenyl)tetrahydrofuran (RR,SS and RS,SR)

The (RR,SS)-isomers are prepared from the evaporation residue of (RR,SS)-isomers obtained in Example 4(b) according to the procedure described in Example 2. The product is recrystallized from isopropanol. The yield is 16.2 g (49% from desoxybenzoin) and the product has m.p. 116°–8° C.

¹H-NMR-spectrum (CDCl₃): δ1.90–2.60 (2H, m), 3.77 (3H, s), 3.80–4.50 (3H, m), 6.85 (2H, d), 7.02 (10H, s), 7.52 (2H, d).

MS: m/z 330 (M+, 13), 212 (85), 135 (87), 118 (93), 117 (100), 100 (44), 91 (42), 77 (50).

The (RS,SR)-isomers are prepared from 34.8 g of (RS,SR)-1,2-diphenyl-1-(4-methoxyphenyl)butane-1,4-diol in the same manner as (RR,SS)-isomers above, after which a mixture of (RS,SR)- and (RR,SS)-isomers is obtained. The evaporation residue is recrystallized from isopropanol. The precipitate consisting of (RR,SS)-isomers is removed by filtration. The mother liquor is evaporated and the evaporation residue is recrystallized from methanol. The yield of the product is 4.6 g (14%) having m.p. 74°–6° C.

¹H-NMR-spectrum (CDCl₃): δ1.95–2.60 (2H, m), 3.64 (3H, s), 3.80–4.55 (3H, m), 6.54 (2H, d), 6.90–7.45 (10H, m), 7.59 (2H, dd).

EXAMPLE 6

(a) 1,2-diphenyl-1-(4-methoxyphenyl)-1-buten-4-ol (Z and E)

(Z)-isomer: (Z)-1,2-diphenyl-1-(4-hydroxyphenyl)-1-buten-4-ol (See Example 13a) is dissolved in methanol, after which an excess of diazomethane is added. When the reaction is completed the solvent is evaporated. The recrystallization is performed from petrol ether. The yield is almost quantitative and the product has m.p. 121°–3° C.

¹H-NMR-spectrum (CDCl₃): δ1.28 (1H, s), 2.73 (2H, t), 3.57 (2H, t), 3.65 (3H, s), 6.53 (2H, d), 6.80 (2H, d), 7.15, (5H, s), 7.29 (5H, s).

MS: m/z 330 (M+, 79), 299 (100), 221 (46), 191 (70), 121 (46), 91 (60).

(E)-isomer: the product is prepared from (E)-1,2-diphenyl-1-(4-hydroxyphenyl)-1-buten-4-ol (see Example 13a) in the same manner as the corresponding (Z)-isomer. The m.p. is 107°–10° C.

¹H-NMR-spectrum (CDCl₃): δ1.31 (1H, s), 2.80 (2H, t), 3.61 (2H, t), 3.81 (3H, s), 6.80–7.35 (14H, m).

(Z,E)-isomer mixture: The reaction is performed under dry conditions. First 34.8 g of 1,2-diphenyl-1-(4-methoxyphenyl)butane-1,4-diol are dissolved in 200 ml of acetic acid anhydride. Then 30 ml of acetyl chloride are added. The mixture is kept for 2 h at 100° C., after which the solvent is evaporated. (The intermediate is pure (Z,E)-4-acetoxy-1,2-diphenyl-1-(4-methoxyphenyl)-1-butene.) Then 200 ml of 94% ethanol, 20 ml of water and 45 ml of 20% sodium hydroxide solution are added to the evaporation residue. The mixture is refluxed for 1 h. The solution is neutralized with 2M hydrochloric acid, after which the ethanol is evaporated. Water is added to the residue and the product is extracted in ethyl acetate. The ethyl acetate solution is dried over sodium sulfate and the solvent is evaporated. The yield of the pure mixture of the isomers (Z:E 7:3), m.p. 91°–105° C., is quantitative. The evaporation residue is recrystallized from a mixture of hexane and ethanol (95:5), and 14.5 g (44%) of (Z)-isomer are obtained.

(b) 4-bromo-1,2-diphenyl-1(4-methoxyphenyl)-1-butene (Z)

33.0 g of (Z)-1,2-diphenyl-1-(4-methoxyphenyl)-1-buten-4-ol are dissolved in 500 ml of dry acetonitrile. Then 39.3 g of triphenylphosphine and 49.8 g of carbon tetrabromide are added while stirring. The stirring is continued for 1 h at room temperature. The solvent is evaporated and the evaporation residue is dissolved in hot petrol ether. The insoluble material is removed by filtration. The mother liquor is evaporated, and the evaporation residue is recrystallized from methanol. The yield of the product is 26.7 g (68%) having m.p. 116°–8° C.

$^1$H-NMR-spectrum (CDCl$_3$): δ3.01 (2H, t), 3.28 (2H, t), 3.67 (3H, s), 6.54 (2H, d), 6.80 (2H, d), 7.17 (5H, s), 7.32 (5H, s).

MS: m/z 392/394 (M+, 86), 299 (65), 221 (79), 191 (94), 121 (100), 91 (50).

EXAMPLE 7

1,2-diphenyl-1-(4-benzyloxyphenyl)butane-1,4-diol (RR,SS; RS,SR)

The (RR,SS; RS,SR)-isomer mixture is prepared from 13.2 g of cinnamaldehyde and 28.8 g of 4-benzyloxybenzophenone according to the precedure described in Example 9. Recrystallization is performed from toluene. The yield is 32.5 g (77%) of a product having m.p. 109°–15° C. The product contains both isomer pairs (RR,SS: RS,SR 1:1).

$^1$H-NMR-spectrum (CD$_3$OD): δ1.88–2.24 (2H, m), ~3.3 (2H, t), 3.85 (1H, t), 4.76 (2H, s), 4.91 (1H, s), 5.07 (1H, s), 6.62 (1H, d), 6.86–7.49 (16H, m), 7.57 (1H, d), 7.65 (1H, dd).

EXAMPLE 8

(a) 1,2-diphenyl-1-(4-benzyloxyphenyl)-1-buten-4-ol (Z and E)

The (Z,E)-isomer mixture is prepared from 42.4 g of 1,2-diphenyl-1-(4-benzyloxyphenyl)butane-1,4-diol (RR, SS: RS, SR 1:1) according to the procedure described in Example 6a. (The intermediate is pure (Z, E)-4acetoxy-1,2-diphenyl-1-(4-benzyloxyphenyl)-1-butene (Z:E, 7:3)).

Isolation of the (Z)-isomer:

After the hydrolysis stage, the precipitate formed is collected by filtration. The precipitate is recrystallized from toluene-petrol ether (1:1), and 15.1 g (37%) of the (Z)-isomer are obtained, m.p. 141°–3° C.

$^1$H-NMR-spectrum (CDCl$_3$): δ 1.30 (1H, s), 2.73 (2H, t), 3.57 (2H, t), 4.90 (2H, s), 6.60 (2H, d), 6.81 (2H, d), 7.15 (5H, s), 7.30 (5H, s), 7.31 (5H, s).

MS: m/z 406 (M+, 28), 91 (100)

Isolation of the (E)-isomer:

After filtration of the hydrolysis solution another precipitate is formed, which is also collected by filtration. Recrystallization of the precipitate from toluene-petrol ether (1:4) gives 2.0 g (5%) of the (E)-isomer, m.p. 96°–8° C.

$^1$H-NMR-spectrum (CDCl$_3$): δ 1.30 (1H, s), 2.79 (2H, t), 3.59 (2H, t), 5.05 (2H, s), 6.84–7.47 (19H, m)

MS: m/z 406 (M+, 5), 91 (100)

(b) 4-chloro-1,2-diphenyl-1-(4-benzyloxyphenyl)-1-butene (Z and E)

(Z)-isomer: 40.6 g of (Z)-1,2-diphenyl-1-(4-benzyloxyphenyl)-1-buten-4-ol are dissolved in 400 ml of dry acetonitrile. Then 32.8 g of triphenylphosphine and 76.9 g of carbontetrachloride are added. The mixture is refluxed 1 h. On cooling, the product precipitates and is filtered off and recrystallized from ethanol. The yield is 39.5 g (93%) of a product having m.p. 115°–6° C./128°–9° C.

$^1$H-NMR-spectrum (CDCl$_3$): δ 2.91 (2H, t), 3.41 (2H, t), 4.91 (2H, s), 6.60 (2H, d), 6.81 (2H, d), 7.16 (5H, s), 7.32 (10H, s)

MS: m/z 424/426 (M+, 7/4), 91 (100)

(E)-isomer: The (E)-isomer is prepared in the same manner as the (Z)-isomer above. The product is recrystallized from methanol. The yield is 35.2 g (83%) of a product m.p. 91°–3° C.

$^1$H-NMR-spectrum (CDCl$_3$): δ 2.97 (2H, t), 3.43 (2H, t), 5.06 (2H, s), 6.83–7.48 (19H, m)

EXAMPLE 9

(a) 1,2-diphenyl-1-[4-[2-(N,N-dimethylamino)ethoxy]-phenyl]-butane -1,4-diol (RR, SS and RS, SR)

The reaction is performed under dry conditions. 2.1 g of lithium aluminium hydride and 50 ml of dry tetrahydrofuran are placed in a flask. Then 13.2 g of cinnamaldehyde in 50 ml of dry tetrahydrofuran are added while stirring and keeping the temperature at 25°–35° C. The stirring is continued for another 30 min at room temperature. Then 26.9 g of 4-[2-(N,N-dimethylamino)-ethoxy]benzophenone in 70 ml of dry tetrahydrofuran are added while stirring.

The temperature is kept at 35°–45° C. during the addition. After stirring for 2 h at 40° C. the reaction mixture is poured into 150 ml of 25% ammonium chloride solution, and aluminium hydroxide is precipitated and filtered off.

The filtrate is transferred to a separating funnel and the organic layer is separated. The aqueous layer is once again extracted with 60 ml of ethyl acetate. The organic layers are combined and dried over sodium sulfate. The solvent is evaporated. The residue is recrystallized from toluene. The yield is 27.5 g (68%). The product contains both (RR, SS)- and (RS, SR)-isomer pairs, the (RR, SS)-pair being enriched because of differences in solubility.

Isolation of the (RR, SS)-isomers:

Recrystallizing the product above from acetone gives 13.8 g (34%) of the (RR, SS)-isomer pair, m.p. 165°–7° C. (from toluene).

$^1$H-NMR-spectrum (CD$_3$OD): δ 2.07 (2H, q), 2.33 (6H, s), 2.76 (2H, t), 3.34 (2H, t), 3.86 (1H, dd), 4.10 (2H, t), 4.76 (2H, s), 6.80–7.25 (12H, m), 7.58 (2H, d).

Isolation of the (RS, SR)-isomers:

The acetone mother liquor above is evaporated. Recrystallizing the residue twice from acetone gives 5.3 g (13%) of the (RS, SR)-isomer pair, m.p. 139°–41° C. (from toluene).

¹H-NMR-spectrum (CD₃OD): δ 2.03 (2H, q), 2.27 (6H, s), 2.64 (2H, t), 3.32 (2H, t), 3.86 (1H, t), 3.93 (2H, t), 4.76 (2H, s), 6.56 (2H, d), 6.95–7.45 (10H, m), 7.66 (2H, dd).

(b)
2,3-diphenyl-2-[4-[2-(N,N-dimethylamino)ethoxy]-phenyl]-tetrahydrofuran (RR, SS)

The compound is prepared from 40.5 g of (RR, SS)-1,2-diphenyl-1-[4-[2-(N,N-dimethylamino)ethoxy]-phenyl]-butane-1,4-diol in the same manner as 2,2,3-triphenyl-tetrahydrofuran in Example 2 except that 15 ml of concentrated sulfuric acid is used instead of 10 ml. Recrystallization is performed from ethanol. The yield of the product is 29.8 g (77%) having m.p. 83°–5° C.

¹H-NMR-spectrum (CDCl₃): δ 1.90–2.50 (2H, m), 2.30 (6H, s), 2.68 (2H, t), 4.02 (2H, t), 3.85–4.50 (3H, m), 6.87 (2H, d), 7.02 (10H, s), 7.51 (2H, d).

MS: m/z 387 (M⁺, 2%), 269 (5%), 117 (22), 91 (7), 72 (10), 58 (100).

EXAMPLE 10

(a)
4-acetoxy-1,2-diphenyl-1-[4-[2-(N,N-dimethylamino)ethoxy]-phenyl]-1-butene (Z,E)

The reaction is performed under dry conditions. 40.5 g of either (RR, SS)- or (RS, SR)-1,2-diphenyl-1-[4-[2-(N,N-dimethylamino)ethoxy]phenyl]butane-1,4-diol and 150 ml of acetic acid anhydride are placed in a flask. The temperature is raised to 90° C., where it is kept until the primary OH-group is completely acetylated. [4-acetoxy-1,2-diphenyl-1-[4-[2-(N,N-dimethylamino)ethoxy]phenyl]butan-1-ol is obtained as intermediate; m.p. of the (RR, SS)-isomer pair is 97°–9° C.]. While stirring the reaction mixture, 30 ml of acetyl chloride in 50 ml of acetic acid anhydride are added at 90° C. The stirring is continued at this temperature for 2 h. The solvent is evaporated. Then 1M sodium carbonate solution is added in excess, after which the product is extracted in toluene. The solution is dried over sodium sulfate, and the solvent is evaporated. The yield of the pure isomer mixture (Z:E 2:1) is quantitative. The m.p. of the (Z)-isomer is 67°–9° C. prepared from the corresponding (Z)-alcohol by refluxing in acetic acid.

(b)
1,2-diphenyl-1-[4-[2-(N,N-dimethylamino)ethoxy]-phenyl]-1-buten-4-ol (Z and E)

Route 1: The compound is prepared from 44.7 g of (Z,E) 4-acetoxy-1,2-diphenyl-1-[4-[2-(N,N-dimethylamino)-ethoxy]phenyl]-1-butene (Z:E 2:1) in the same manner as 1,1,2-triphenyl-1-buten-4-ol in Example 3b. The yield of the pure mixture of the isomers (Z:E 2:1), m.p. 93°–100° C., is quantitative.

Route 2: Either 40.5 g of 1,2-diphenyl-1-[4-[2-(N,N-dimethylamino)ethoxy]phenyl]butane-1,4-diol or 38.7 g of 2,3-diphenyl-2-[4-[2-(N,N-dimethylamino)ethoxy]-phenyl]-tetrahydrofuran (either (RR, SS)- or (RS, SR)-isomer pair) are dissolved in 250 ml of dry ethanol containing an excess of hydrogen chloride gas. The mixture is refluxed for 1 h and the solvent is then evaporated. A mixture of the (Z)- and (E)-isomers as hydrochloride salts is obtained. The base can be liberated from the salt, for example in the following way. The evaporation residue is suspended in 1M sodium carbonate solution, after which the free base is extracted in ethyl acetate. The ethyl acetate solution is dried over sodium sulfate and the solvent is evaporated. The yield of the mixture of the isomers (Z:E 2:1) is quantitative, but the mixture contains as impurity about 5% of 2,3-diphenyl-2-[4-[2-(N,N-dimethylamino) ethoxy]phenyl]tetrahydrofuran.

Route 3: Either 40.5 g of 1,2-diphenyl-1-[4-[2-(N,N-dimethylamino)ethoxy]phenyl]butane-1,4-diol or 38.7 g of 2,3-diphenyl-2-[4-[2-(N,N-dimethylamino)ethoxy]-phenyl]tetrahydrofuran (either (RR,SS)- or (RS, SR)-isomers) are dissolved in 250 ml of hot concentrated hydrochloric acid. The mixture is stirred for 15 min at 90°–100° C. The cooled mixture is neutralized with 48% sodium hydroxide solution, after which the product is extracted in ethyl acetate. Then the ethyl acetate solution is dried over sodium sulfate and the solvent is evaporated. The yield of the mixture of isomers (Z:E 1:2) is quantitative, but the mixture contains as impurity about 5% of 2,3-diphenyl-2-[4-[2-(N,N-dimethylamino)ethoxy]-phenyl]tetrahydrofuran.

Isolation of the (Z)-isomer as a free base: The mixture of the isomers (Z:E 2:1) from route (1) is recrystallized from toluene, and 15.9 g (41%) of the (Z)-isomer is obtained, m.p. 110°–2° C.

¹H-NMR-spectrum (CDCl₃): δ 2.23 (6H, s), 2.60 (2H, t), 2.71 (2H, t), 3.53 (2H, t), 3.89 (2H, t), 6.53 (2H, d), 6.78 (2H, d), 7.12 (5H, s), 7.28 (5H, s).

Isolation of the (Z)-isomer as the hydrochloride salt: The mixture of the isomers (Z:E 2:1) from Route 1 is dissolved in ethanol and an excess of concentrated hydrochloric acid is added. The solvent is evaporated, and the residue is recrystallized twice from ethanol. 12.3 g (29%) of (Z)-isomer as the hydrochloride salt is obtained, m.p. 166°–8° C. (from acetone). The hydrochloride salt of the (Z)-isomer can also be prepared from the (Z)-isomer base for example in the following way. The (Z)-isomer is dissolved in ethanol. Then hydrogen chloride gas is passed into the solution. Finally the solvent is evaporated.

Isolation of the (E)-isomer: The mother liquors obtained in the isolation of the hydrochloride salt of the (Z)-isomer are combined and the solvent is evaporated. The evaporation residue is recrystallized from acetone, and 9.7 g (23%) of the hydrochloride salt of the (E)-isomer are obtained, m.p. 235°–7° C. The (E)-isomer can be liberated from the salt by the same method as with the mixture of isomers. The m.p. of the (E)-isomer as a free base is 129°–31° C. (from toluene).

¹H-NMR-spectrum (CDCl₃): δ 2.31 (6H, s) 2.71 (2H, t), 2.78 (2H, t), 3.57 (2H, t), 4.05 (2H, t), 6.87 (2H, d), 6.94 (5H, s), 7.10 (5H, s), 7.21 (2H, d).

(c)
4-chloro-1,2-diphenyl-1-[4-[2-(N,N-dimethylamino)ethoxy]-phenyl]-1-butene (Z and E)

(Z)-isomer: The reaction is performed under dry conditions. 42.4 g of (Z)-1,2-diphenyl-1-[4-[2-(N,N-dimethylamino)ethoxy]phenyl]-1-buten-4-ol are dissolved in 250 ml of chloroform. Then 23.8 g of thionyl chloride are added dropwise. The mixture is refluxed 3 h. The solvent is evaporated, after which the product is recrystallized from ethyl acetate. The yield of the hydrochloride salt is 36.7 g (83%), m.p. 194°–6° C. The base can be liberated from the salt with 1M sodium carbonate solution, after which the base is extracted in toluene. The toluene solution is dried and the solvent is evaporated. The free base has m.p. 108°–10° C. (from acetone).

$^1$H-NMR-spectrum (CDCl$_3$): δ 2.27 (6H, s), 2.63 (2H, t), 2.91 (2H, t), 3.41 (2H, t), 3.92 (2H, t), 6.54 (2H, d), 6.79 (2H, d), 7.15 (5H, s), 7.31 (5H, s).

MS: m/z 405/407 (M+, 7/3), 72 (20), 58 (100).

The citric acid salt can be prepared as follows: 40.6 g of the (Z)-isomer as a free base are dissolved in 175 ml of warm acetone and 24.3 g of citric acid are dissolved in 100 ml of warm acetone. The solutions are combined and the mixture is allowed to cool. The citrate, m.p. 160°–162° C., is collected by filtration.

(E)-isomer: The compound is prepared from (E)-1,2-diphenyl-1-[4-[2-(N,N-dimethylamino)ethoxy]phenyl]-1-buten-4-ol in the same manner as the corresponding (Z)-isomer. The hydrochloride salt is crystallized from toluene. The yield is 35.8 g (81%) of a product having m.p. 183°–5° C. The base can be liberated from the salt in the same manner as the corresponding (Z)-isomer. It has m.p. 69°–71° C. (from hexane).

$^1$H-NMR-spectrum (CDCl$_3$): δ 2.34 (6H, s), 2.74 (2H, t), 2.97 (2H, t), 3.43 (2H, t), 4.08 (2H, t), 6.80–7.30 (14H, m).

MS: m/z 405/407 (M+, 7/3), 72 (19), 58 (100).

EXAMPLE 11

(a) 4-benzyloxy-1,2-diphenylbutan-1-one

This compound is prepared from 19.6 g of desoxybenzoin and 21.5 g of benzylether-protected bromoethanol according to the procedure described in Example 1(a).

(b) 4-benzyloxy-1,2-diphenyl-1-[4-[(tetrahydropyran-2-yl)oxy]phenyl]butan-1-ol (RR, SS)

The compound is prepared from the evaporation residue obtained in step (a) and 38.6 g of tetrahydropyran-2-yl ether-protected 4-bromophenol according to the procedure described in Example 1(b).

(c) 4-benzyloxy-1,2-diphenyl-1-(4-hydroxyphenyl)butan-1-ol (RR, SS)

The compound is prepared from the evaporation residue obtained in step (b) according to the procedure described in Example 1(c).

(d) 1,2-diphenyl-1-(4-hydroxyphenyl)-butane-1,4-diol (RR, SS)

The evaporation residue obtained in step (c) is dissolved in 300 ml of 94% ethanol. Then 2 g of 5% palladium-on-charcoal are added. The reaction mixture is stirred at room temperature under a hydrogen atmosphere until one equivalent of hydrogen is consumed. The catalyst is filtered off. The solvent is evaporated, and the residue is crystallized from toluene. The yield is 12.7 g (38% from desoxybenzoin) of a product having m.p. 192°–4° C.

$^1$H-NMR-spectrum (CD$_3$OD): δ 2.08 (2H, q), 3.34 (2H, t), 3.83 (1H, dd), 4.76 (3H, s), 6.76 (2H, d), 6.85–7.25 (10H, m), 7.47 (2H, d).

EXAMPLE 12

2,3-diphenyl-2-(4-hydroxyphenyl)tetrahydrofuran (RR, SS and RS, SR)

The (RR, SS)-isomers are prepared from 33.4 g of (RR, SS)-1,2-diphenyl-1-(4-hydroxyphenyl)butane-1,4-diol according to the procedure described in Example 2. Ethyl acetate is used as solvent in the extraction stage. The product is recrystallized from isopropanol. The yield after drying is 28.1 g (89%) of a product having m.p. 137°–40° C.

$^1$H-NMR-spectrum (CD$_3$OD): δ 1.85–2.60 (2H, m), 3.80–4.45 (3H, m), 4.79 (1H, s), 6.75 (2H, d), 7.01 (10H, s), 7.44 (2H, d).

MS: 316 (M+, 6), 121 (25), 118 (100), 117 (52).

The (RS, SR)-isomers: The solvent of the isopropanol mother liquor above is evaporated. The evaporation residue is recrystallized from toluene, after which (RS, SR)-isomers, m.p. 119°–132° C., are obtained in low yield.

$^1$H-NMR-spectrum (CD$_3$OD): δ 1.85–2.50 (2H, m), 3.75–4.45 (3H, m), 4.75 (1H, s), 6.41 (2H, d), 6.80–7.45 (10H, m), 7.62 (12H, dd).

EXAMPLE 13

(a) 1,2-diphenyl-1-(4-hydroxyphenyl)-1-buten-4-ol (Z and E).

Route 1: 31.6 g of 2,3-diphenyl-2-(4-hydroxyphenyl)-tetrahydrofuran are dissolved in 125 ml of acetic acid, after which 25 ml of 40% of hydrogenbromide in acetic acid are added. The mixture is stirred for 1 h at 75° C. The solvent is evaporated. [The intermediate is the 4-acetoxy-1-butene derivative.] The evaporation residue is dissolved in a mixture containing 200 ml of 94% ethanol, 20 ml of water and 60 ml of 20% sodium hydroxide solution. Then the mixture is refluxed for 1 h. The solution is neutralized with 2M hydrochloric acid after which the ethanol is evaporated. Water is added to the residue and the product is extracted in ethyl acetate. The ethyl acetate solution is dried over sodium sulfate and the solvent is evaporated. The evaporation residue is treated with charcoal in methanol.

The methanol is evaporated and the product crystallized from toluene. The yield of the pure mixture of the isomers (Z:E 1:1), m.p. 164°–7° C., is 22.8 g (72%).

Route 2: 33.0 g of 2,3-diphenyl-2-(4-methoxyphenyl)-tetrahydrofuran are dissolved in 100 ml of acetic acid after which 50 ml of 40% hydrogenbromide in acetic acid are added. The mixture is refluxed for 2 h. Then 50 ml of 40% hydrogenbromide in acetic acid are added and the refluxing is continued for another 2 h. The solvent is evaporated. (The intermediate is the 4-acetoxy-1-butene derivative). The hydrolysis of the ester and the purification is performed according to the method in Route 1 above. Th yield of the pure mixture of the isomers (Z:E 1:1) is 11.7 g (37%).

Isolation of the (E)-isomer: 20.0 g of the mixture of the isomers are dissolved in warm methylene chloride, and then an excess of 2M sodium hydroxide solution is added. After thorough mixing, the mixture is filtered. The precipitate, which is the (E)-isomer as a sodium salt, is suspended in 2M hydrochloric acid. The (E)-isomer is then extracted as the free phenol in ethyl acetate. The ethyl acetate solution is dried over sodium sulfate and the solvent is evaporated.

Finally the (E)-isomer is recrystallized from water-methanol (50:50). The yield is 7.2 g (36%) of a product having m.p. 165°–7° C.

$^1$H-NMR-spectrum (CD$_3$COCD$_3$): δ 2.78 (2H, t), 3.54 (2H, t), 6.83 (2H, d), 6.90–7.35 (12H, m), 8.32 (1H, s).

MS: m/z 316 (M+, 64), 285 (100), 207 (87), 191 (58), 107 (55), 91 (94).

The sodium salt can be prepared as described above. Another method comprises dissolving the pure (E)-isomer in ethanol, adding an equivalent amount of sodium hydroxide in ethanol and evaporating the solvent. Finally the sodium salt is washed with acetone. It has m.p. 216°–26° C.

Isolation of the (Z)-isomer: The sodium hydroxidemethylene chloride mother liquor is transferred to a separating funnel. The methylene chloride layer is removed. The water layer is neutralized with concentrated hydrochloric acid and then extracted with ethyl acetate. The ethyl acetate solution is dried over sodium sulfate and the solvent is evaporated. Finally (Z)-isomer is recrystallized from water-methanol (50:50). The yield is 6.2 g (31%) of a product having m.p. 169°–71° C.

$^1$H-NMR-spectrum (CD$_3$COCD$_3$): δ 2.70 (2H, t), 3.52 (2H, t), 6.48 (2H, d), 6.74 (2H, d), 7.15 (5H, s), 7.32 (5H, s), 8.08 (1H, s).

MS: m/z 316 (M+, 35), 285 (38), 207 (54), 191 (37), 107 (50), 91 (100).

The sodium salt of the (Z)-isomer is prepared as described for the (E)-isomer. It has m.p. 205°–217° C.

(b)
4-chloro-1,2-diphenyl-1-(4-hydroxyphenyl)-1-butene (Z and E).

(Z)-isomer: 42.5 g of (Z)-4-chloro-1,2-diphenyl-1-(4-benzyloxyphenyl)-1-butene are dissolved in 800 ml of the mixture of ethyl acetate and ethanol (1:1). Then 4 g of 5% palladium-on-charcoal are added. The reaction mixture is stirred at room temperature under a hydrogen atmosphere until one equivalent of hydrogen is consumed. The catalyst is filtered off. The solvent is evaporated, and the product is washed with petrol ether. The yield is quantitative and the product has m.p. 84°–7° C. (from methanol).

$^1$H-NMR-spectrum (CD$_3$OD): δ 2.87 (2H, t), 3.38 (2H, t), 4.76 (1H, s), 6.42 (2H, d), 6.70 (2H, d), 7.15 (5H, s), 7.30 (5H, s).

MS: m/z 334/336 (M+, 94/32, 285 (71), 207 (78), 191 (56), 183 (100), 107 (55), 91 (86).

(E)-isomer: The (E)-isomer is prepared in the same manner as (Z)-isomer above. The product is washed with petrol ether. The yield is nearly quantitative, m.p. 109°–12° C.

$^1$H-NMR-spectrum (CD$_3$OD): δ 2.96 (2H, t), 3.42 (2H, t), 4.79 (1H, s), 6.79 (2H, d), 6.93 (5H, s), 7.12 (2H, d), 7.12 (5H, s).

EXAMPLE 14

4-chloro-1,2-diphenyl-1-(4-hydroxyphenyl)butane (RR, SS and RS, SR)

(RR, SS)-isomers are prepared from 42.5 g of (Z)-4-chloro-1,2-diphenyl-1-(4-benzyloxyphenyl)-1-butene according to the procedure described in Example 13 (b) except that 10% palladium-on-charcoal and 800 ml ethanol as solvent are used. The reaction is stopped when two equivalents of hydrogen have been consumed. After evaporation of the solvent the product is washed with petrol ether and recrystallized from methanol. It melts at 118°–20° C.

$^1$H-NMR-spectrum (CDCl$_3$): δ 1.62–2.37 (2H, m), 2.94–3.43 (2H, m), 3.66 (1H, td), 4.08 (1H, d), 4.64 (1H, s), 6.77 (2H, d), 7.03 (5H, s), 7.12 (5H, s), 7.28 (2H, d).

MS: m/z 336/338 (M+1, 1/0.4), 183 (100), 165 (13), 91 (14).

The benzoate is prepared from the (RR, SS)-isomers as follows. 0.4 g TBAH is dissolved in 5 ml of water. Then 3 ml of 20% sodium hydroxide solution and 3.4 g of the (RR, SS)-isomers are added. The mixture is stirred 10 min at room temperature. After that 1.7 g of benzoylchloride in 30 ml of chloroform is added. The mixture is stirred 2 h at room temperature.

Methylene chloride is added. After shaking, the water layer is removed and the organic layer is washed with water. The organic solution is dried over sodium sulfate and the solvent is evaporated. The evaporation residue is washed with methanol. The yield is quantitative of a product having m.p. 202°–5° C.

The (RS, SR)-isomers are prepared from corresponding (E)-isomer in the same manner as the (RR, SS)-isomers above. The product is recrystallized from petrol ether. The yield is 62% of a product having m.p. 133°–6° C.

$^1$H-NMR-spectrum (CDCl$_3$): δ 1.78–2.21 (2H, m), 2.94–3.44 (2H, m), 3.69 (1H, td), 4.08 (1H, d), 4.48 (1H, br s), 6.48 (2H, d), 6.96 (2H, d), 7.14 (5H, s), 7.33 (5H, br s).

The benzoate is prepared from the (RS, SR)-isomers as above and recrystallized from methanol. The yield is 88% of a product having m.p. 128°–31° C.

EXAMPLE 15

(a)
4-[(tetrahydropyran-2-yl)oxy]-1,2-bis[[4-(tetrahydropyran-2-yl)oxy]phenyl]butan-1-one.

The compound is prepared from 39.6 g of 4,4'-bis[(tetrahydropyran-2-yl)oxy]desoxybenzoin and 20.9 g of tetrahydropyran-2-yl ether-protected bromoethanol according to the procedure described in Example 1(a).

(b)
4-[(tetrahydropyran-2-yl)oxy]-1-phenyl-1,2-bis[[4-(tetrahydropyran-2-yl)oxy]phenyl]butan-1-ol (RS, SR)

The compound is prepared from the evaporation residue obtained in step (a) and 23.6 g of bromobenzene according to the procedure described in Example 1(b).

(c) 1-phenyl-1,2-bis(4-hydroxyphenyl)butane-1,4-diol (RS, SR)

The compound is prepared from the evaporation residue obtained in step (b) according to the procedure described in Example 1(c). The product is recrystallized from toluene. The yield is 8.4 g (24% from 4,4'-bis[(tetrahydropyran-2-yl)oxy]-desoxybenzoin) of a product having m.p. 213°–5° C.

EXAMPLE 16

2-phenyl-2,3-bis(4-hydroxyphenyl)tetrahydrofuran (RR, SS)

The compound is prepared from the evaporation residue obtained in Example 15(b) in the same way as 2,2,3-triphenyltetrahydrofuran in Example 2, except that the extraction is performed with ethyl acetate instead of toluene. The product is recrystallized from toluene. The yield is 14.9 g (45% from 4,4'-bis[(tetrahydropyran-2-yl)-oxy]desoxybenzoin) of a product having m.p. 194°–6° C.

$^1$H-NMR-spectrum (CD$_3$OD): δ 1.90–2.45 (2H, m), 3.80–4.45 (3H, m), 4.75 (2H, s), 6.48 (2H, d), 6.72 (2H, d), 6.83 (2H, d), 6.80–7.15 (5H, m), 7.41 (2H, d).

MS: m/z 332 (M+, 4), 134 (100).

EXAMPLE 17

5-hydroxy-1,2-diphenylpentan-1-one

Method 1: A mixture containing 19.6 g desoxybenzoin, 13.9 g of 3-bromopropan-1-ol, 1 g TBAH, 40 ml of 48% sodium hydroxide solution and 60 ml toluene is stirred for 24 h at 45° C. Water is added and the product extracted in toluene. The toluene solution is washed with water and dried over sodium sulfate. Finally the solvent is evaporated. The yield is nearly quantitative, but the product contains about 10–15% of the O-alkylation product. M.p. of the chromatographically purified sample is 45°–8° C.

$^1$H-NMR-spectrum (CD$_3$OCD$_3$): δ 1.30–2.49 (4H, m), 2.82 (1H, s), 3.55 (2H, t), 4.82 (1H, t), 7.03–7.64 (8H, m), 8.04 (2H, dd).

Method 2: In the first stage 19.6 g of desoxybenzoin is alkylated with 15.8 g of 3-bromo-1-chloropropane according to the procedure described in method 1 except that the reaction is carried out at room temperature. Isolation gives an intermediate, 2,3-diphenyl-4,5-dihydro-6H-pyran in quantitative yield, but the product contains about 10% of noncyclic O-alkylation product. The m.p. of a sample which has been chromatographically purified and recrystallized from methanol is 119°–22° C.

$^1$H-NMR-spectrum (CDCl$_3$): δ 1.87–2.17 (2H, m), 2.48 (2H, t), 4.16 (2H, dd), 7.02–7.55 (10H, m).

In the second stage the crude intermediate is first dissolved in 900 ml of ethanol. Then 100 ml of water and 5 ml of concentrated sulfuric acid are added. The mixture is stirred for 3 days at room temperature. The cyclic intermediate hydrolyses to 5-hydroxy-1,2-diphenylpentan-1-one. The reaction mixture is neutralized with 2M sodium hydroxide solution and the solvent is evaporated. The residue is extracted with toluene. The toluene solution is washed with water and dried over sodium sulfate. Then the solvent is evaporated. The evaporation residue is treated with hot petrol ether, which dissolves the noncyclic O-alkylation product from the first stage. After the mixture has cooled, the solvent is decanted to leave the pure product as an oil. The yield is 20.1 g (79%).

EXAMPLE 18

1,1,2-triphenylpentane-1,5-diol

The compound is prepared from 6.0 g of magnesium turnings in 42 ml of dry tetrahydrofuran, 39.3 g of bromobenzene in 84 ml of dry tetrahydrofuran and 25.4 g of 5-hydroxy-1,2-diphenylpentan-1-one in 75 ml of dry tetrahydrofuran according to the procedure described in Example 1(b). The product is recrystallized from toluene. The yield is 14.9 g (45%) of a product having m.p. 120°–2° C.

$^1$H-NMR-spectrum (CD$_3$OD): δ 1.12–1.52 (2H, m), 1.75–2.12 (2H, m), 3.40 (2H, t), 3.71 (1H, t), 4.78 (2H, s), 6.90–7.44 (13H, m), 7.65 (2H, dd).

EXAMPLE 19

(a) 5-acetoxy-1,1,2-triphenyl-1-pentene

The compound is prepared from 33.2 g of 1,1,2-triphenylpentane-1,5-diol according to the procedure described in Example 10a. The product is recrystallized from methanol. The yield is 22.1 g (62%) of a product having m.p. 80°–1° C.

$^1$H-NMR-spectrum (CDCl$_3$): δ 1.49–1.89 (2H, m), 1.94 (3H, s), 2.44–2.62 (2H, m), 3.96 (2H, t), 6.95 (5H, br s), 7.12 (5H, s), 7.27 (5H, br s).

(b) 1,1,2-triphenyl-1-penten-5-ol

The compound is prepared from 35.6 g of 5-acetoxy-1,1,2-triphenyl-1-pentene according to the procedure described in Example 3b. The product is recrystallized from toluene-petrol ether. The yield is 12.6 g (40%) of a product having m.p. 128°–30° C.

$^1$H-NMR-spectrum (CDCl$_3$): δ 1.30 (1H, s), 1.44–1.79 (2H, m), 2.44–2.63 (2H, m), 3.51 (2H, t), 6.96 (5H, br s), 7.13 (5H, s), 7.30 (5H, br s).

MS: m/z 314 (M+, 34), 268 (13), 205 (25), 191 (60), 167 (42), 105 (21), 91 (100).

EXAMPLE 20

(a)

5-[(tetrahydropyran-2-yl)oxy]-1,2-diphenylpentan-1-one

The compound is prepared from 19.6 g of desoxybenzoin and 22.3 g of tetrahydropyran-2-yl ether-protected 3-bromopropanol according to the procedure described in Example 1(a).

(b)

5-[(tetrahydropyran-2-yl)oxy]-1,2-diphenyl-1-[[4-(tetrahydropyran-2-yl)oxy]phenyl]pentan-1-ol (RR,SS)

The compound is prepared from the evaporation residue obtained in step (a) and 38.6 g of tetrahydropyran-2-yl ether-protected 4-bromophenol according to the procedure described in Example 1(b).

(c) 1,2-diphenyl-1-(4-hydroxyphenyl)pentane-1,5-diol (RR,SS)

The compound is prepared from the evaporation residue obtained in step (b) by the same method as 1,1,2-triphenylbutane-1,4-diol in Example 1(c).

The product is recrystallized from toluene. The yield is 11.1 g (32% from desoxybenzoin) of a product having m.p. 182°–4° C.

$^1$H-NMR-spectrum (CD$_3$OD): δ 1.10–1.60 (2H, m), 1.65–2.15 (2H, m), 3.38 (2H, t), 3.61 (1H, dd), 4.80 (3H, s), 6.72 (2H, d), 6.80–7.25 (10H, m), 7.39 (2H, d).

EXAMPLE 21

2,3-diphenyl-2-(4-hydroxyphenyl)tetrahydropyran (RR,SS)

The compound is prepared from the evaporation residue obtained in Example 20(b) by the same method as 2,2,3-triphenyltetrahydrofuran in Example 2. Ethyl acetate is used in the extraction. The evaporation residue is recrystallized from isopropanol to give the tetrahydropyran derivative. The yield is 7.3 g (22% from desoxybenzoin) of a product having m.p. 194°–6° C.

$^1$H-NMR-spectrum (CD$_3$OD): δ 0.95–1.35 (1H, m), 1.55–2.60 (3H, m), 3.55–4.30 (3H, m), 4.80 (1H, s), 6.65–7.55 (14H, m).

MS: m/z 330 (M+, 13), 198 (38), 121 (57), 104 (100).

EXAMPLE 22

(a) 1,2-diphenyl-1-(4-hydroxyphenyl)-1-penten-5-ol (Z and E)

The isopropanol mother liquor obtained in Example 21 is evaporated. The evaporation residue is recrystallized from toluene. A mixture of pentenol derivatives (Z:E 1:1) is obtained. The yield is 5.6 g (17% from desoxybenzoin) of a product having m.p. 157°–63° C.

The isomers are separated by the procedure described for their homologs in Example 13a.

The (E)-isomer is recrystallized from water-methanol (2:3). M.p. is 167°–9° C.

¹H-NMR-spectrum (CD₃OD): δ 1.36–1.74 (2H, m), 2.44–2.67 (2H, m), 3.42 (2H, t), 4.75 (2H, s), 6.76 (2H, d), 6.91 (5H, br s), 7.05 (2H, d), 7.09 (5H, s).

MS: m/z 330 (M+, 100), 285 (39), 207 (73), 183 (89), 107 (57), 91 (90).

The (Z)-isomer is recrystallized from water-methanol (1:2). Its m.p. is 164°–7° C.

¹H-NMR-spectrum (CD₃OD): δ 1.35–1.72 (2H, m), 2.37–2.57 (2H, m), 3.39 (2H, t), 4.74 (2H, s), 6.40 (2H, d), 6.68 (2H, d), 7.12 (5H, s), 7.26 (5H, br s).

MS: m/z 330 (M+, 100), 285 (19), 207 (70), 183 (97), 115 (76), 91 (81).

(b)
5-acetoxy-1,2-diphenyl-1-(4-hydroxyphenyl)-1-pentene (Z,E)

The isomer mixture (Z:E 1:1) is prepared from the corresponding alcohol mixture (Z:E 1:1) by ester exchange reaction with ethyl acetate using concentrated hydrochloric acid as catalyst.

¹H-NMR-spectrum (CD₃OD): δ 1.34–1.69 (2H, m), 1.79 (1.5H, s), 1.83 (1.5H, s), 2.29–2.56 (2H, m), 3.79 (1H, t), 3.83 (1H, t), 4.67 (1H, s), 6.30 (1H, d), 6.59 (1H, d), 6.67 (1H, d), 6.94 (1H, d), 6.81–7.24 (10H, m).

EXAMPLE 23

5-chloro-1,2-diphenylpentan-1-one

The compound is prepared from 19.6 g of desoxybenzoin, which is alkylated with 15.8 g of 3-bromo-1-chloropropane according to the procedure described in Example 17, method 1, except that the reaction time is only 15 min at room temperature. The product is recrystallized from methanol. The yield is 16.6 g (61%) of a product having m.p. 72°–4° C.

¹H-NMR-spectrum (CDCl₃): δ 1.54–2.56 (4H, m), 3.50 (2H, t), 4.56 (1H, t), 7.21–7.50 (8H, m), 7.94 (2H, dd).

EXAMPLE 24

(a)
5-chloro-1,2-diphenyl-1-[[4-(tetrahydropyran-2-yl)oxy]phenyl]pentan-1-ol (RR,SS)

A Grignard complex is prepared under dry conditions by reacting 3.6 g of magnesium turnings in 50 ml of dry tetrahydrofuran with 38.6 g of tetrahydropyran-2-yl ether-protected 4-bromophenol in 75 ml of dry tetrahydrofuran. Then two thirds of the complex solution is added into a boiling mixture containing 27.3 g of 5-chloro-1,2-diphenylpentan-1-one and 100 ml of dry tetrahydrofuran. Then the complex solution is added portion-wise until all or nearly all the starting material has reacted, as shown by thin-layer chromatography of a sample of the reaction mixture. The reaction mixture is then refluxed for 1 h. The isolation is performed in the same manner as in Example 1(b).

(b)
5-chloro-1,2-diphenyl-1-(4-hydroxyphenyl)pentan-1-ol (RR,SS)

The compound is prepared from the evaporation residue obtained in step (a) according to the procedure described in Example 1(c) except that only 5 g of concentrated sulfuric acid is used. A small sample is purified, by recrystallization from toluene-petrol ether, and then has m.p. 75°–8° C.

¹H-NMR-spectrum (CD₃OD): δ 1.30–1.77 (2H, m), 1.85–2.15 (2H, m), 3.37 (2H, t), 3.64 (1H, dd), 4.60 (2H, s), 6.78 (2H, d), 6.88–7.22 (10H, m), 7.45 (2H, d).

EXAMPLE 25

5-chloro-1,2-diphenyl-1-(4-hydroxyphenyl)-1-pentene (Z)

The evaporation residue obtained in Example 24(b) is dissolved in 300 ml of ethanol, after which 10 ml of concentrated hydrochloric acid is added. The mixture is refluxed for 30 min. The solution is treated with charcoal, and filtered. The solvent is evaporated giving a mixture of the (Z)- and (E)-isomers. The isomer mixture is recrystallized from petrol ether to give 7.7 g (22% from 5-chloro-1,2-diphenylpentan-1-one) of the (Z)-isomer, m.p. 116°–8° C.

¹H-NMR-spectrum (CD₃OD): δ 1.56–1.94 (2H, m), 2.47–2.66 (2H, m), 3.35 (2H, t), 4.74 (1H, s), 6.41 (2H, d), 6.69 (2H, d), 7.13 (5H, s), 7.22–7.41 (5H, m).

EXAMPLE 26

4,4-diethoxy-1,2-diphenylbutan-1-one

The compound is prepared from 19.6 g of desoxybenzoin and 19.7 g of bromacetaldehyde diethyl acetal according to the procedure in Example 1(a). The reaction is performed however at 90° C. and using TBAH as catalyst instead of TEBAC.

EXAMPLE 27

(a)
4,4-diethoxy-1,2-diphenyl-1-[4-(2-morpholinoethoxy)phenyl]butan-1-ol

The compound is prepared from the evaporation residue obtained in Example 26 and 42.9 g of 1-bromo-4-(2-morpholinoethoxy)benzene according to the procedure described in Example 1(c).

(b)
5-hydroxy-2,3-diphenyl-2-[4-(2-morpholinoethoxy)phenyl]tetrahydrofuran.

The evaporation residue obtained in step (a) is dissolved in a mixture containing 19.5 g of concentrated sulfuric acid, 150 ml of water and 400 ml of tetrahydrofuran. The mixture is stirred for 3 h at room temperature. The solution is neutralized with 2M sodium hydroxide solution and the solvent is evaporated. The product is extracted in toluene containing ethyl acetate. The solution is dried over sodium sulfate. The solvent is evaporated, and the residue is recrystallized from toluene. The yield is 12.0 g (27% from desoxybenzoin) of a product having m.p. 150°–3° C.

¹H-NMR-spectrum (CDCl₃): δ 2.20–2.55 (2H, m), 2.65 (4H, t), 2.86 (2H, t), 3.78 (4H, t), 4.14 (2H, t), 4.54 (1H, dd), 5.85–6.05 (1H, m), 6.80–7.30 (12H, m), 7.53 (2H, d).

EXAMPLE 28

4-chloro-1,2-diphenyl-1-[4-[2-(N,N-diethylamino)ethoxy]phenyl]-1-butene (Z and E)

43.3 g of 1,2-diphenyl-1-[4-[2-(N,N-diethylamino)ethoxy]phenyl]butane-1,4-diol (pure enantiomer pairs or their mixture; m.p. of (RR,SS)-pair is 107°–9° C.) is suspended in 250 ml of toluene, after which 25 ml toluene is distilled off to dry the solution. The mixture is cooled to 0° C. with stirring. While stirring and keeping the temperature at 0° C. or a little below, 47.6 g of thionyl chloride of good quality are added. The mixture is stirred for 1 h at 0° C. and the temperature is then allowed to rise to 22° C. The mixture is stirred at 80° C. until the reaction is completed (about 3 h). After that, water is added to decompose the excess of thionyl chloride followed by 20% sodium hydroxide solution to liberate the product from its hydrochloride salt. The aqueous layer is discarded and the toluene layer is washed with water. Then the solvent is evaporated to leave a mixture of (Z)- and (E)-isomers (Z:E 7:3) as an oil in quantitative yield.

(Z)-isomer: The (Z)-isomer is isolated from the isomer mixture above as the hydrochloride salt because of the low melting point of the free base. The m.p. of the hydrochloride salt is 178°–80° C. The (Z)-isomer may be freed from its salt by any normal method.

$^1$H-NMR-spectrum (CDCl$_3$): δ 1.01 (6H, t), 2.57 (4H, q), 2.77 (2H, t), 2.91 (2H, t), 3.41 (2H, t), 3.90 (2H, t), 6.53 (2H, d), 6.78 (2H, d), 7.15 (5H, s), 7.31 (5H, s).

(E)-isomer:

$^1$H-NMR-spectrum (CDCl$_3$): δ 1.07 (6H, t), 2.66 (4H, q), 2.89 (2H, t), 2.97 (2H, t), 3.42 (2H, t), 4.07 (2H, t), 6.90–7.20 (10H, m).

EXAMPLE 29

1,2-diphenyl-1-[4-[2-(4-pyrrolidinyl)ethoxy]phenyl]-1-buten-4-ol (Z and E)

A mixture containing 31.6 g of (Z,E)-1,2-diphenyl-1-(4-hydroxyphenyl)-1-buten-4-ol (Z:E 1:1), 25.5 g of 1-(2-chloroethyl)pyrrolidine hydrochloride, 48.3 g of anhydrous potassium carbonate and 500 ml of butanone is refluxed for 3 h, after which inorganic salts are removed by filtration. Then the solvent is evaporated and the evaporation residue is dissolved in a mixture of toluene and ethylacetate (2:1). After washing the organic solution with water and drying it with sodium sulfate, the solvent is evaporated leaving the products as an oil (Z:E 1:1).

(Z)-isomer: The evaporation residue above is transformed into its hydrochloride salt and treated with acetone. The (Z)-isomer hydrochloride salt is precipitated and collected by filtration. The base is liberated from its salt by conventional means and crystallised from toluene-petrol ether (1:1). In this way 15.3 g (37%) of the (Z)-isomer are obtained, m.p. 122°–5° C.

$^1$H-NMR-spectrum (CDCl$_3$): δ 1.65–1.82 (4H, m), 2.55 (4H, t), 2.79 (4H, t), 3.56 (2H, t), 3.95 (2H, t), 6.53 (2H, d), 6.79 (2H, d), 7.14 (5H, s), 7.29 (5H, s).

(E)-isomer: It is isolated from acetone mother liquor above.

$^1$H-NMR-spectrum (CDCl$_3$): δ 1.70–1.89 (4H, m), 2.62 (4H, t), 2.79 (2H, t), 2.89 (2H, t), 3.58 (2H, t), 4.10 (2H, t), 6.80–7.15 (10H, m).

N-oxides of the (Z)-isomer: 4.13 g of the (Z)-isomer, 0.68 g of 50% H$_2$O$_2$ in water, and 40 ml of methanol are stirred for 42 h at room temperature. Water is then added and the precipitate filtered off. The N-oxide melts at 159°–61° C.

We claim:

1. A compound of the formula:

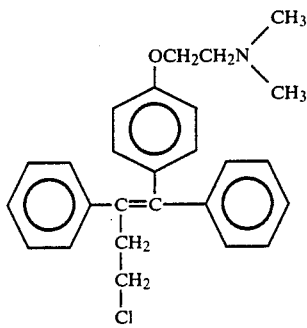

or a non-toxic pharmaceutically acceptable salt or N-oxides thereof.

2. A compound according to claim 1 which is 4-chloro-1,2-diphenyl-1-[4-[2-(N,N-dimethylamino)ethoxy]phenyl]-1-butene or a non-toxic pharmaceutically acceptable salt thereof.

3. A compound according to claim 1 which is the trans-isomer of 4-chloro-1,2-diphenyl-1-[4-[2-(N,N-dimethylamino)ethoxy]phenyl]-1-butene or a non-toxic pharmaceutically acceptable salt thereof.

4. A compound according to claim 1 which is the citrate of the trans-isomer of 4-chloro-1,2-diphenyl-1-[4-[2-(N,N-dimethylamino)ethoxy]phenyl]-1-butene.

5. A pharmaceutical composition suitable for treating hormone-dependent tumours comprising an anti-tumour effective amount of a compound of claim 1 or a non-toxic pharmaceutically acceptable salt thereof and a compatible pharmaceutically carrier therefor.

6. A method of producing an anti-oestrogenic effect in a subject in which such an effect is desired which comprises administering to said subject an anti-oestrogenic effective amount of a compound as defined in claim 3 or a non-toxic pharmaceutically acceptable salt thereof.

7. A method according to claim 6 in which an antioestrogenic effect is produced in a subject suffering from an oestrogen-dependent tumour.

* * * * *

UNITED STATES PATENT AND TRADEMARK OFFICE
CERTIFICATE OF CORRECTION

PATENT NO. : 4,696,949
DATED : September 29, 1987
INVENTOR(S) : Reijo J. TOIVOLA et al.

It is certified that error appears in the above-indentified patent and that said Letters Patent is hereby corrected as shown below:

In the cover page, Item "[75] Inventors":

please correct the spelling of the last-named inventor from "Hannu K. Sunduiqst" to --Hannu K. Sundquist--.

Signed and Sealed this

Eighteenth Day of November 1997

Attest:

BRUCE LEHMAN

Attesting Officer      Commissioner of Patents and Trademarks